United States Patent
Oh

(10) Patent No.: US 9,732,346 B2
(45) Date of Patent: Aug. 15, 2017

(54) SIRNA TARGETING PRK2, WHICH IS HEPATITIS C VIRUS THERAPEUTIC AGENT

(71) Applicant: UNIVERSITY-INDUSTRY FOUNDATION, YONSEI UNIVERSITY, Seoul (KR)

(72) Inventor: Jong-Won Oh, Gyeonggi-do (KR)

(73) Assignee: UNIVERSITY-INDUSTRY FOUNDATION, YONSEI UNIVERSITY (KR)

( * ) Notice: Subject to any disclaimer, the term of this patent is extended or adjusted under 35 U.S.C. 154(b) by 0 days.

(21) Appl. No.: 15/105,516

(22) PCT Filed: Dec. 19, 2014

(86) PCT No.: PCT/KR2014/012561
§ 371 (c)(1),
(2) Date: Jun. 16, 2016

(87) PCT Pub. No.: WO2015/093886
PCT Pub. Date: Jun. 25, 2015

(65) Prior Publication Data
US 2017/0002361 A1  Jan. 5, 2017

(30) Foreign Application Priority Data
Dec. 19, 2013  (KR) .................. 10-2013-0159000

(51) Int. Cl.
*C12N 15/113* (2010.01)
*A61K 31/712* (2006.01)
*A61K 31/7125* (2006.01)
*A61K 31/713* (2006.01)
*A61K 45/06* (2006.01)

(52) U.S. Cl.
CPC ........ *C12N 15/1137* (2013.01); *A61K 31/713* (2013.01); *A61K 45/06* (2013.01); *C12Y 207/11013* (2013.01); *C12N 2310/14* (2013.01); *C12N 2310/315* (2013.01); *C12N 2310/321* (2013.01); *C12N 2310/322* (2013.01); *C12N 2310/3231* (2013.01); *C12N 2310/353* (2013.01); *C12N 2320/31* (2013.01)

(58) Field of Classification Search
None
See application file for complete search history.

(56) References Cited

U.S. PATENT DOCUMENTS 8,076,094 B2 * 12/2011 Schuele ................ C07K 14/47
435/7.21

FOREIGN PATENT DOCUMENTS

| KR | 10-2006-0099558 | 9/2006 |
| KR | 10-2010-0069679 | 5/2008 |
| WO | WO 2010/105372 | 9/2010 |
| WO | WO 2015/093886 | 6/2015 |

OTHER PUBLICATIONS

International Search report for PCT/KR2014/012561 dated Mar. 27, 2015, 5 pages.

\* cited by examiner

*Primary Examiner* — Tracy Vivlemore
(74) *Attorney, Agent, or Firm* — Swanson & Bratschun, L.L.C.

(57) ABSTRACT

The present invention relates to an siRNA targeting PRK2, which is a hepatitis C virus therapeutic agent, and can be effectively used as a hepatitis C virus therapeutic agent since the systemic delivery into a living body, particularly liver cells, is possible through an siRNA targeting a host PRK2 gene, which shows an anti-HCV activity, or a lipid formulation thereof.

14 Claims, 25 Drawing Sheets

[Fig. 1A]
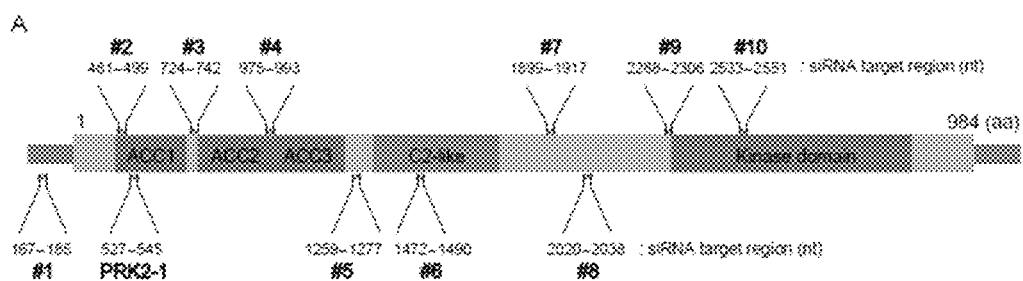
[FIG. 1B]
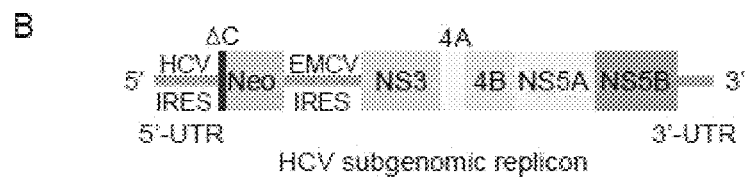
[FIG. 1C]
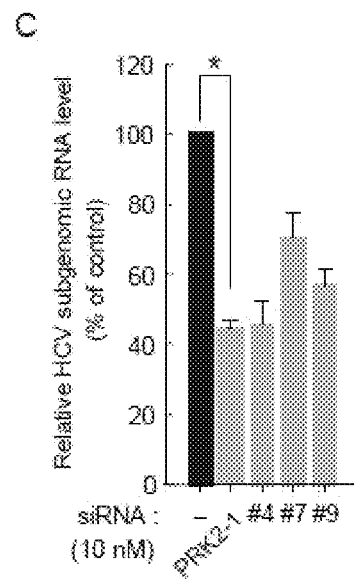

[FIG. 1D]
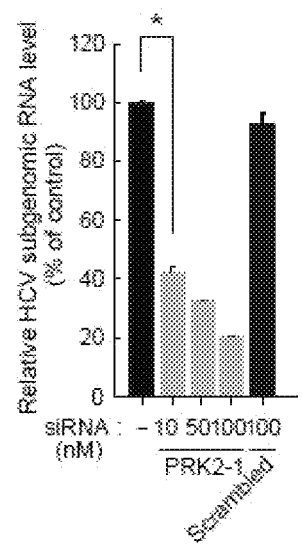
[FIG. 1E]
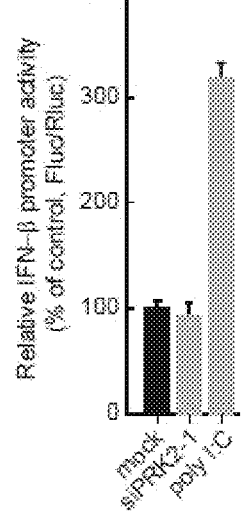

[FIG. 1F]
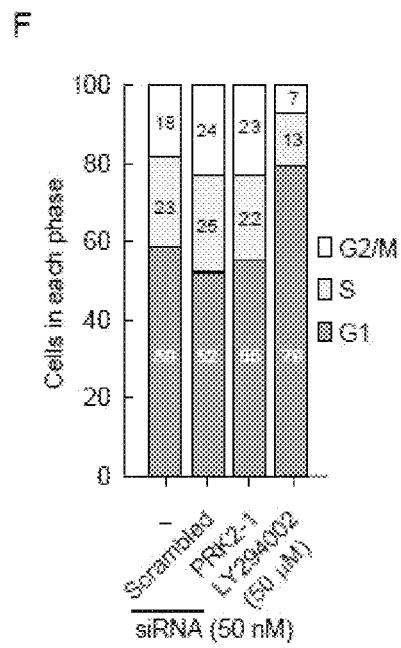
[FIG. 1G]
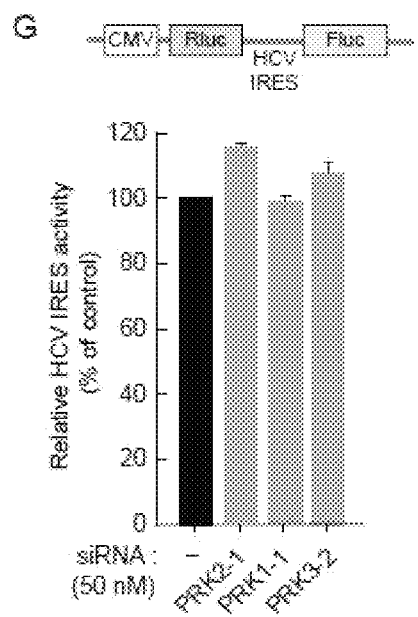

[FIG. 2A]
A
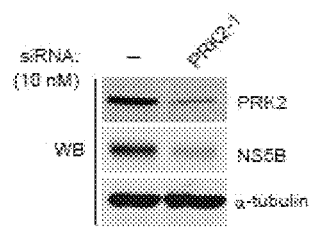
[FIG. 2B]
B
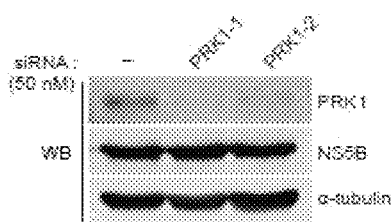
[FIG. 2C]
C
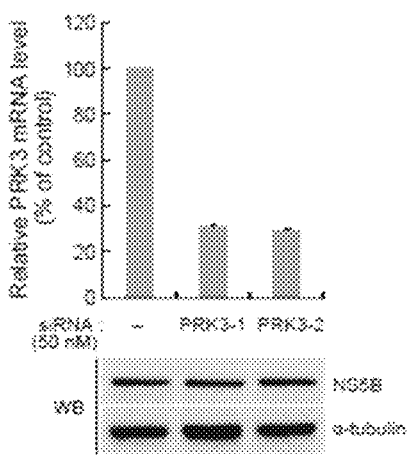

[FIG. 2D]
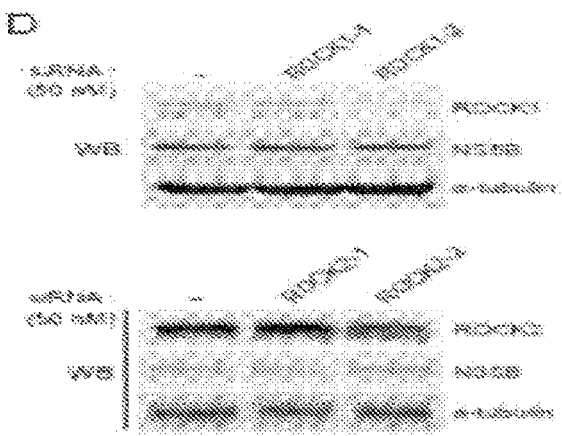
[FIG. 2E]
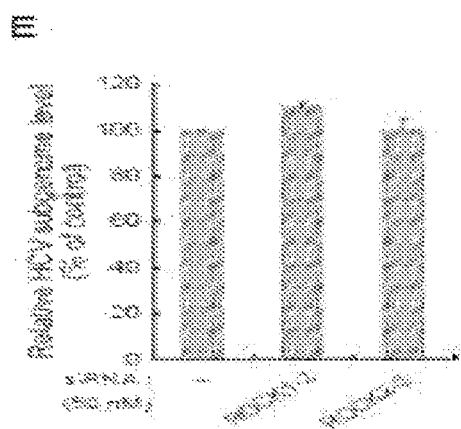
[FIG. 3A]
A
```
PRK1   aa512- V A T W V R L L R R L I    (SEQ ID NO: 23)
PRK2   aa514- I A T W G R L V R R A I    (SEQ ID NO: 24)
PRK3   aa451- M A A W G R L V M N L L    (SEQ ID NO: 25)
Selected peptide   T S T A G R I V R R A I   (SEQ ID NO: 26)
```

[FIG. 3B]
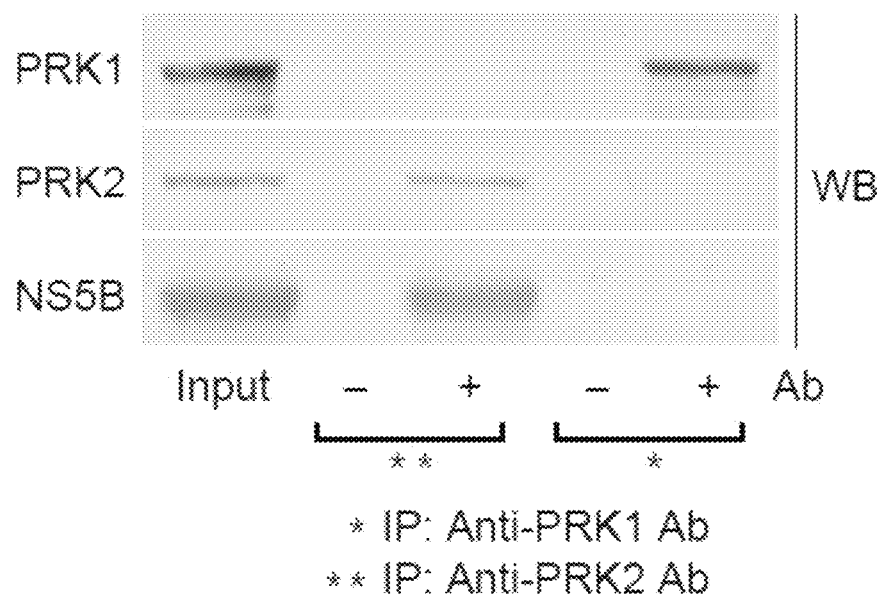
[FIG. 4]
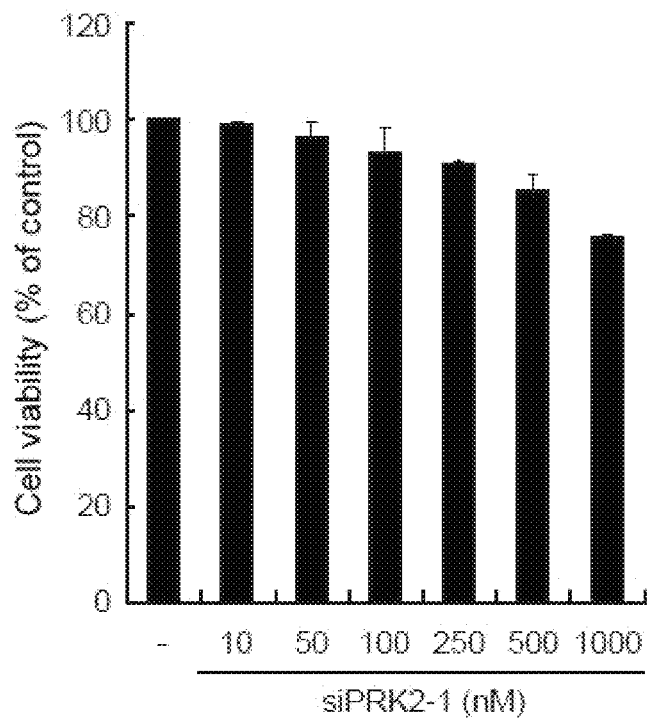

[FIG. 5A]
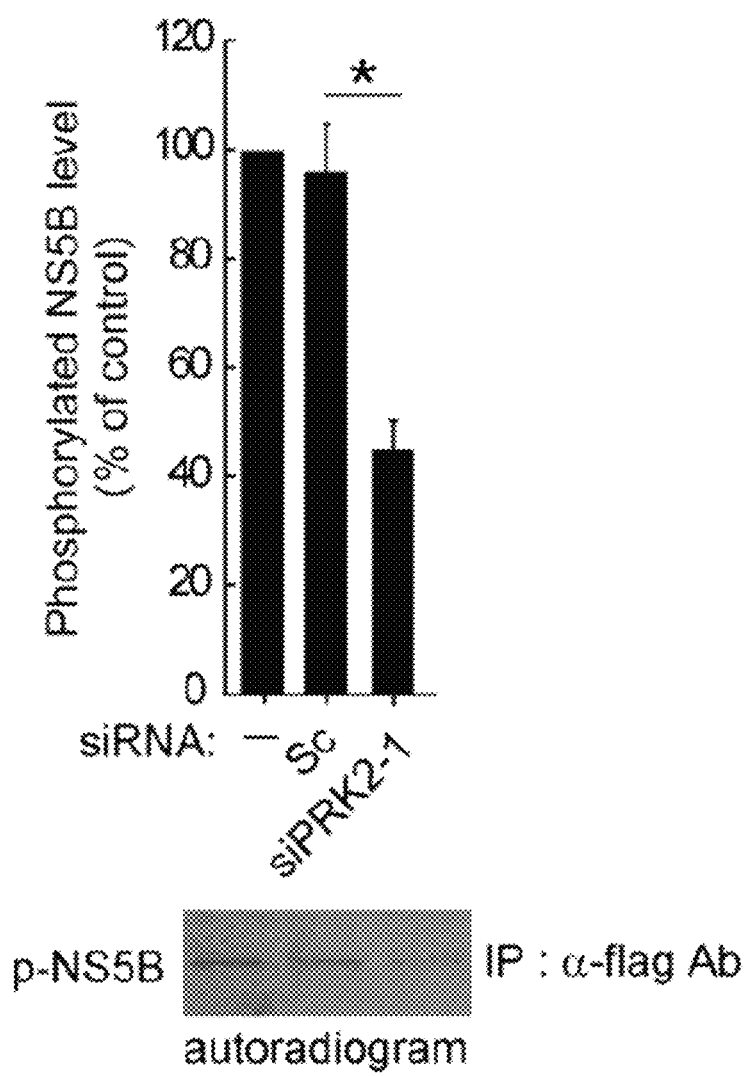

[FIG. 5B]
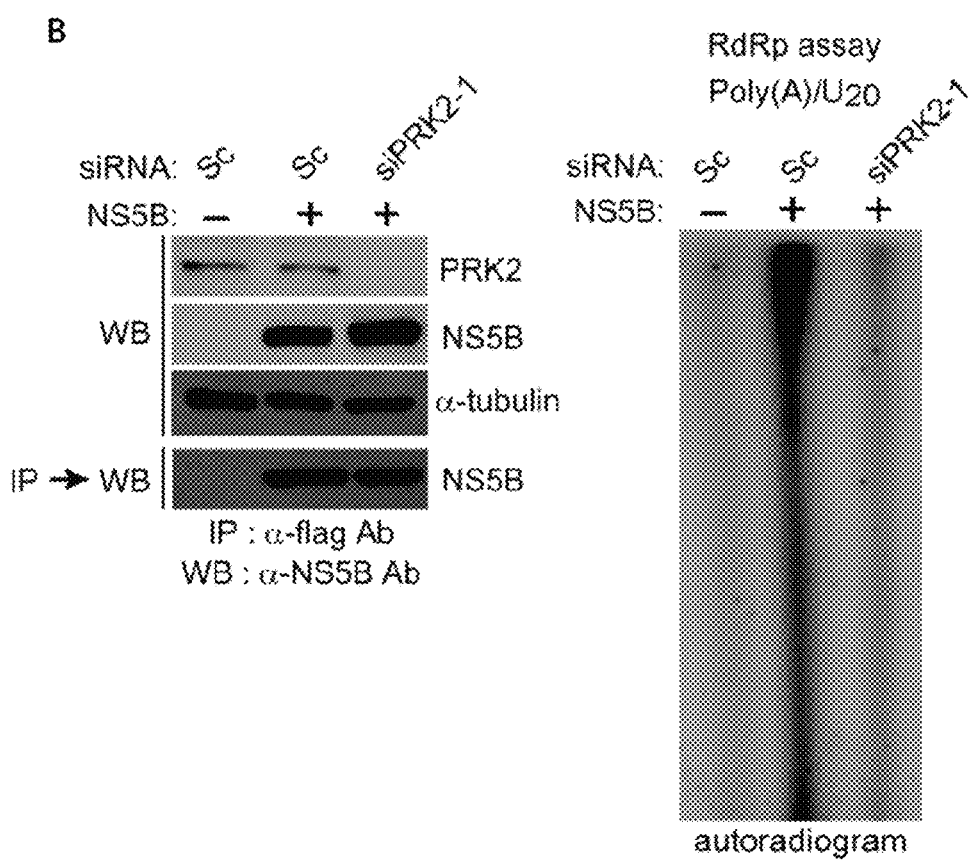
[FIG. 5C]
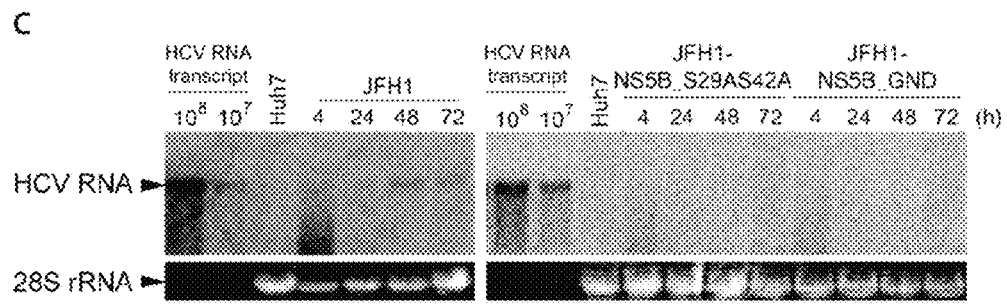

[FIG. 6A]
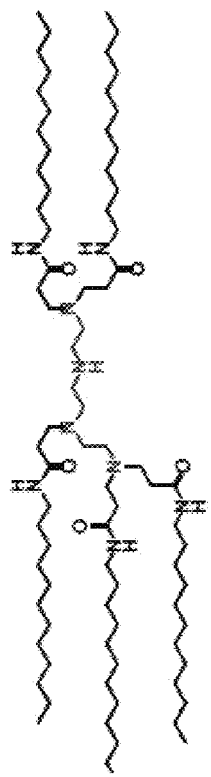

[FIG. 6B]
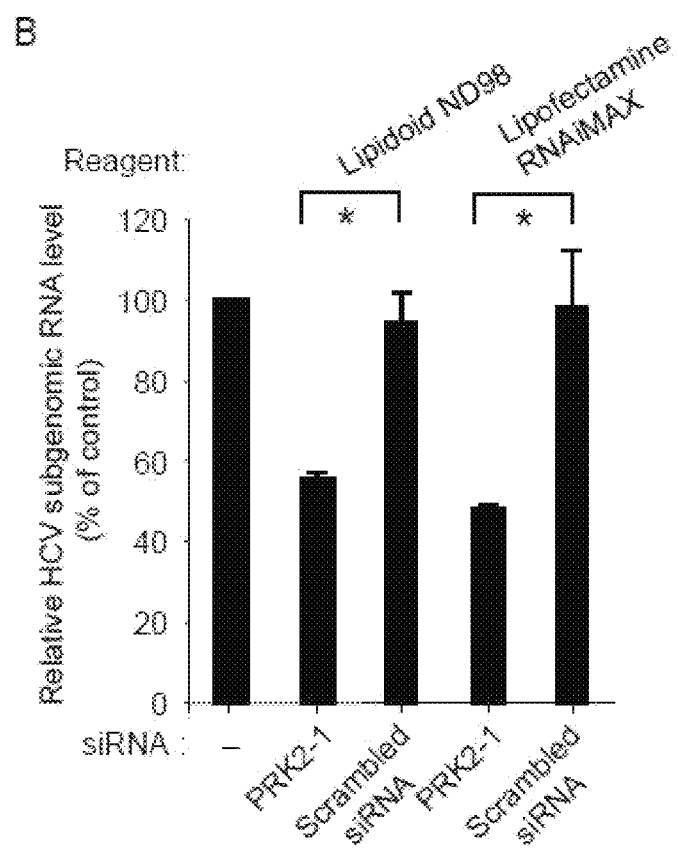

[FIG. 6C]
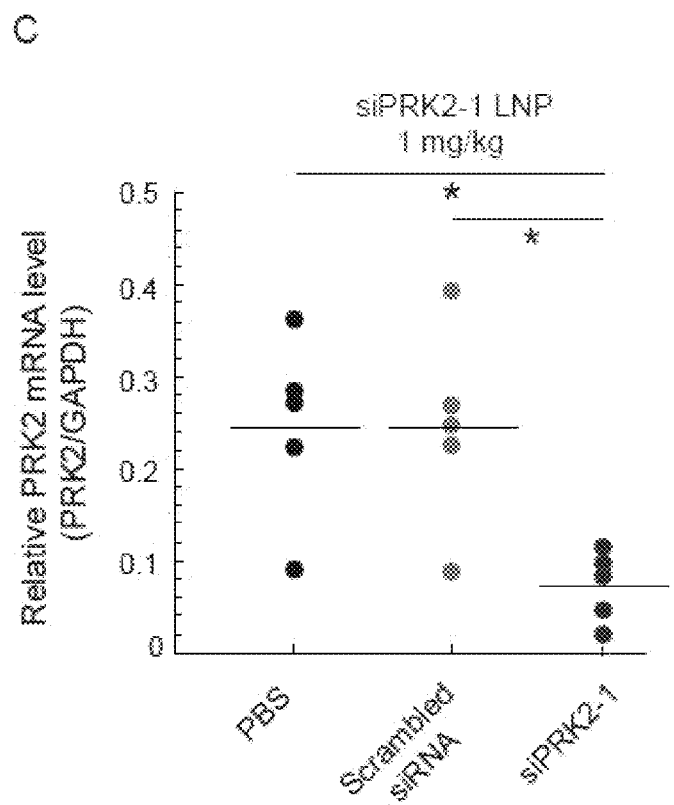

[FIG. 7A]
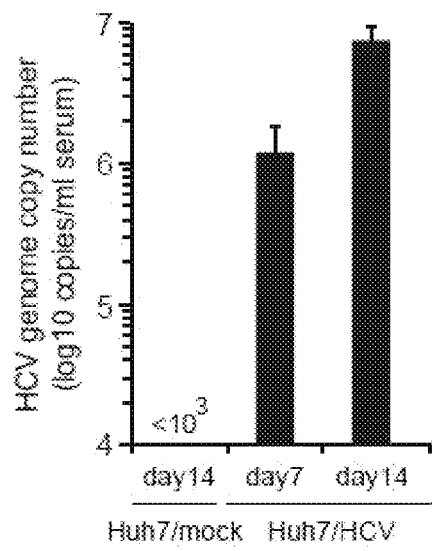
[FIG. 7B]
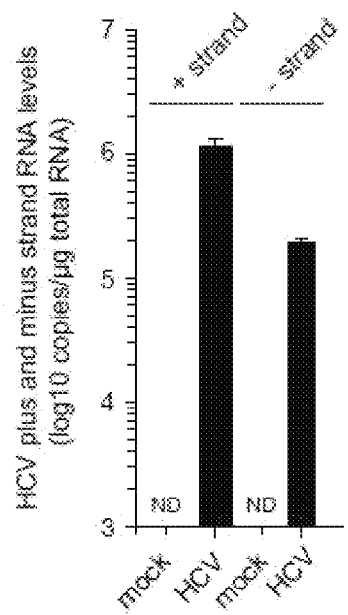

[FIG. 7C]
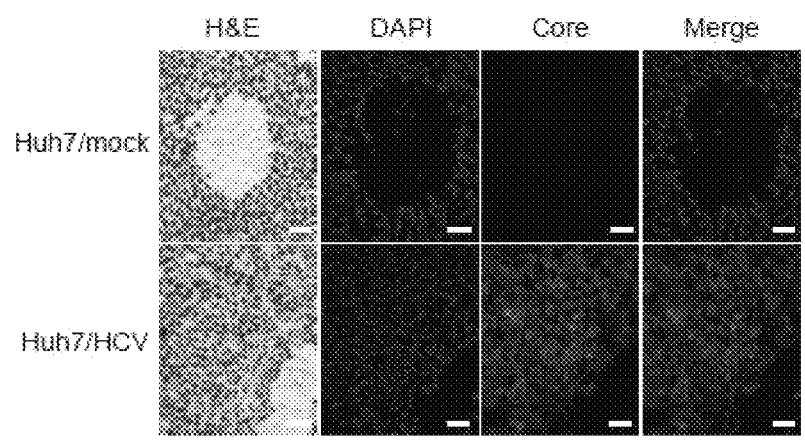
[FIG. 7D]
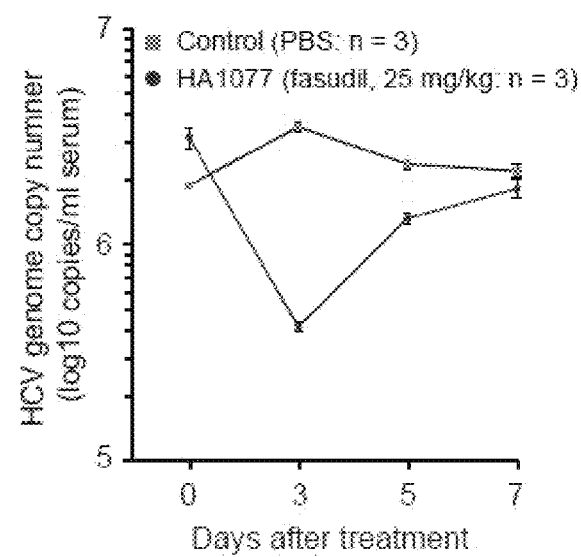

[FIG. 7E]
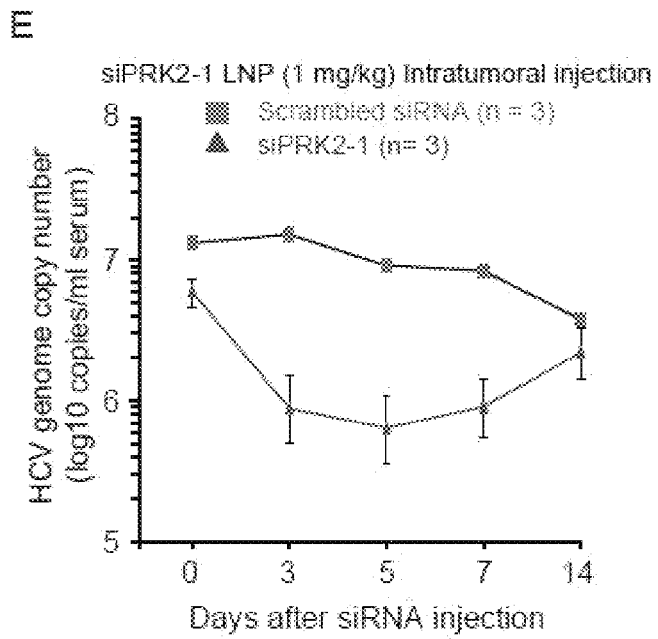
[FIG. 7F]
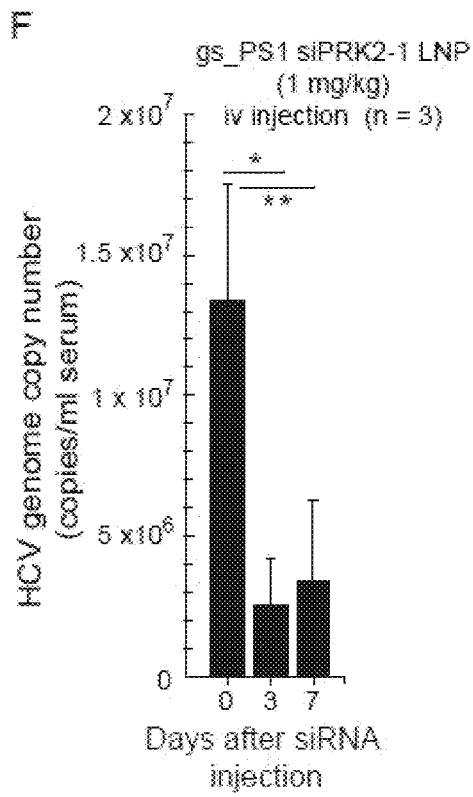

[FIG. 8A]
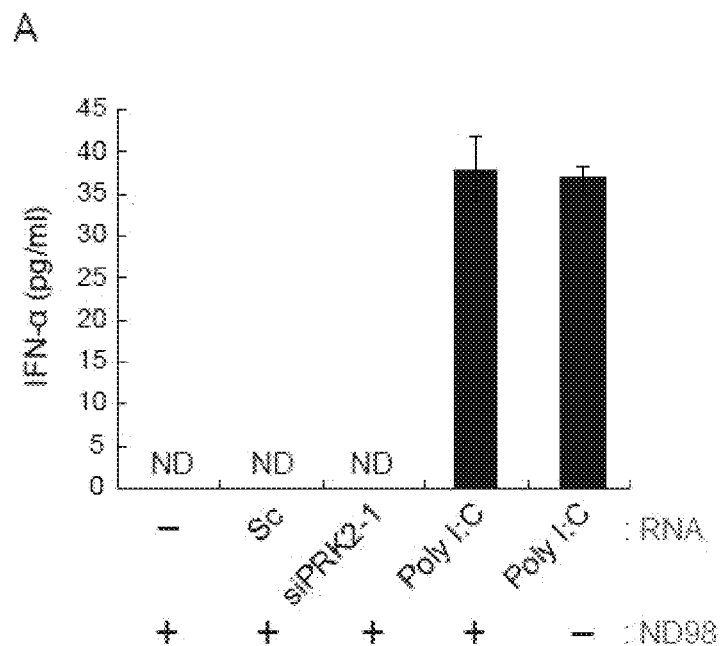
[FIG. 8B]
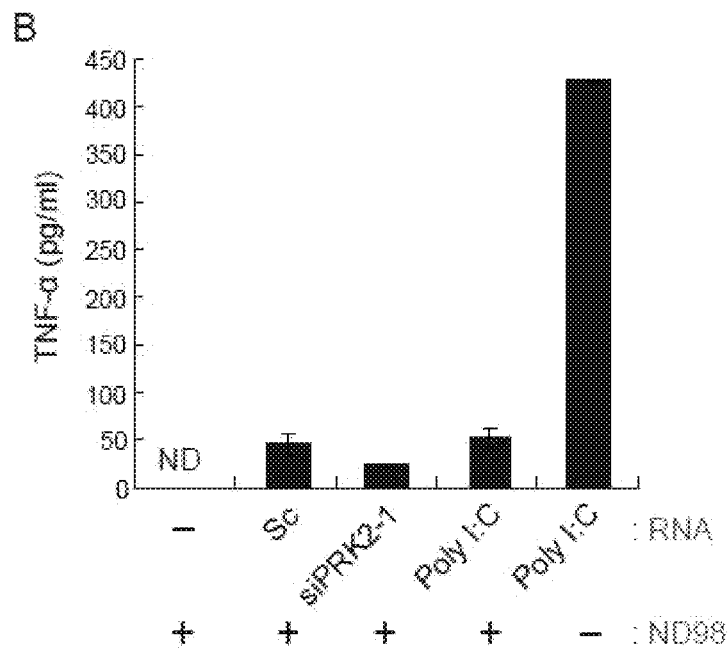

[FIG. 8C]
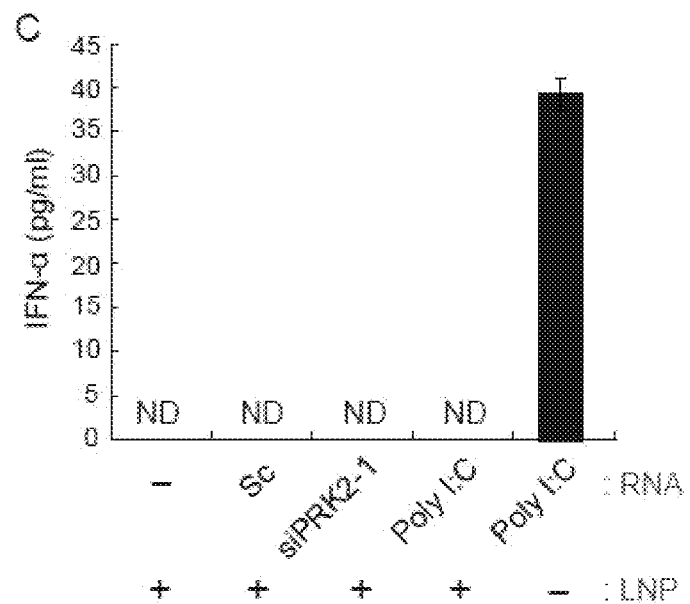
[FIG. 8D]
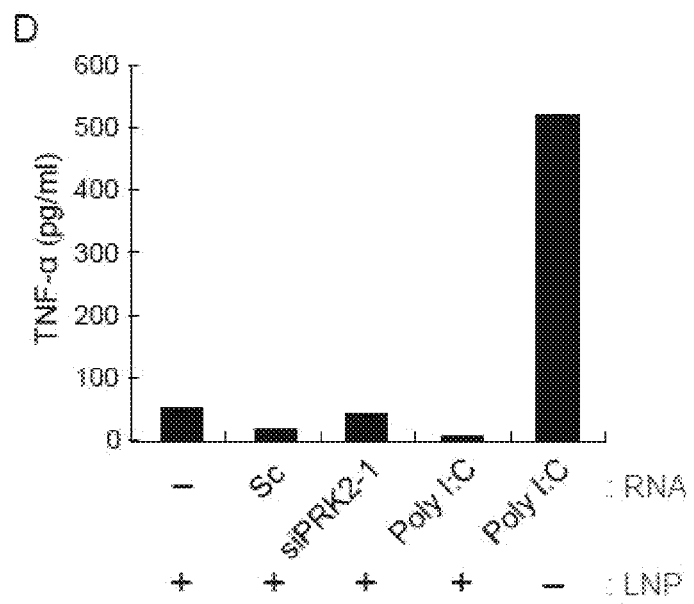

[FIG. 9A]
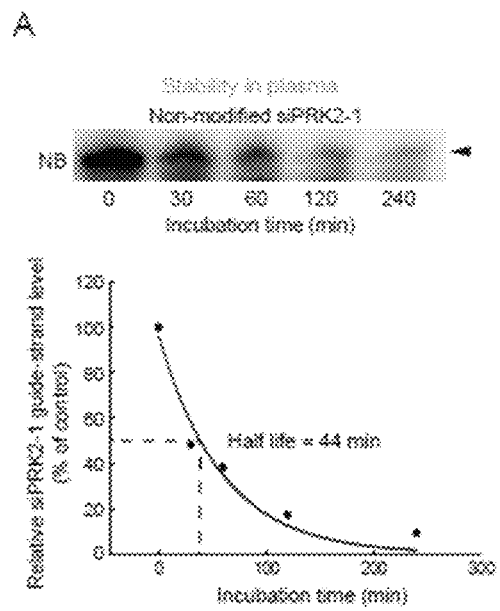
[FIG. 9B]
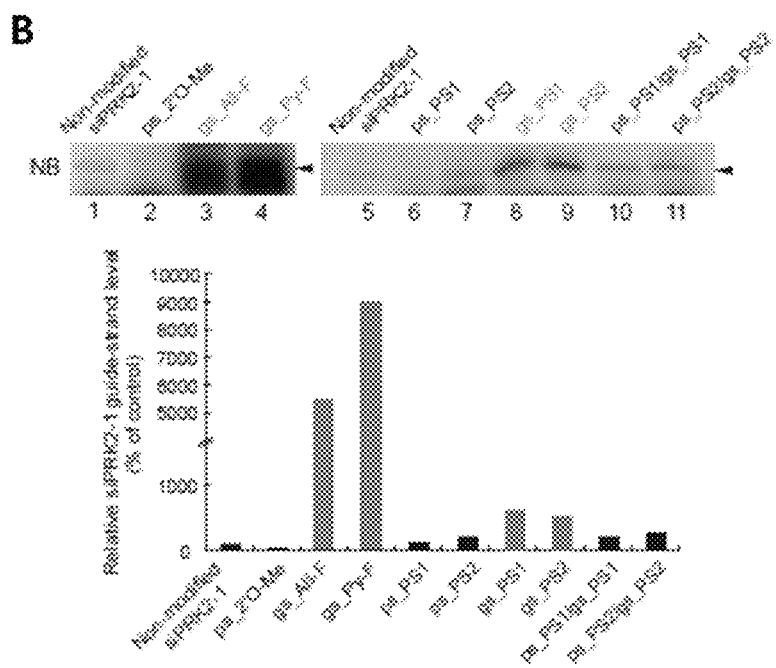

[FIG. 9C]
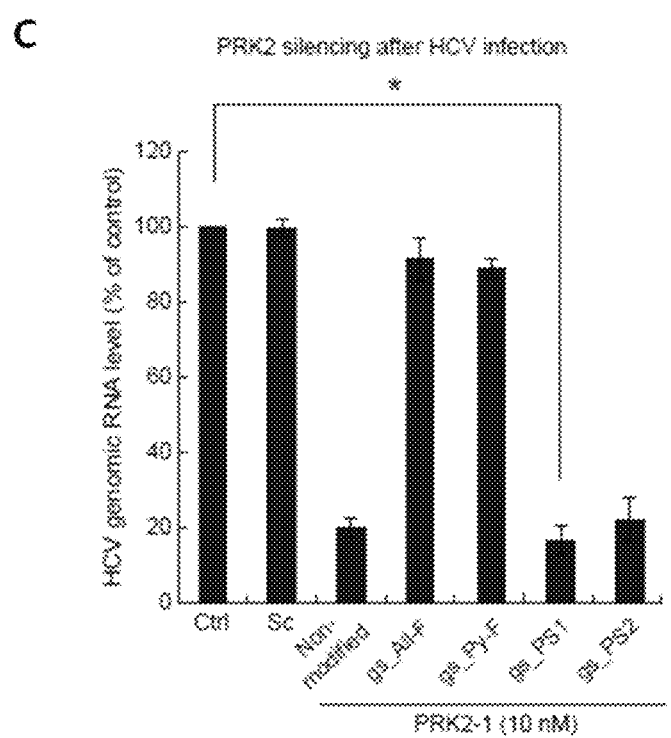

[FIG. 9D]
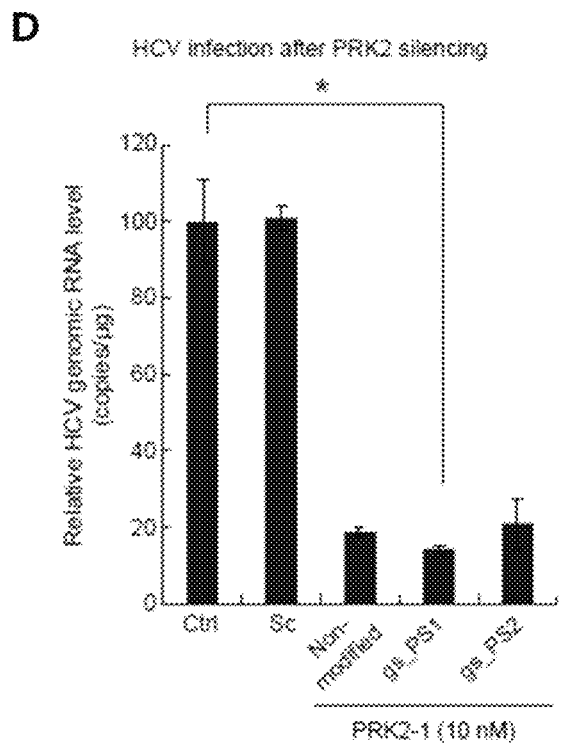
[FIG. 10A]
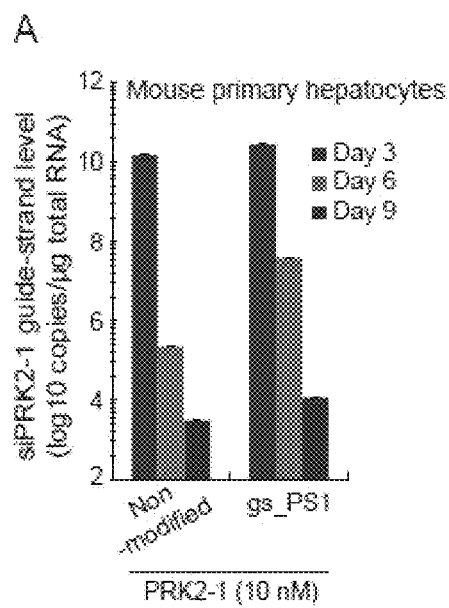

[FIG. 10B]
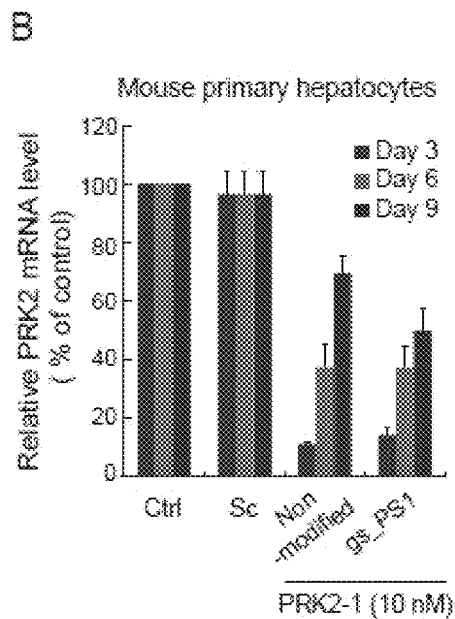
[FIG. 10C]
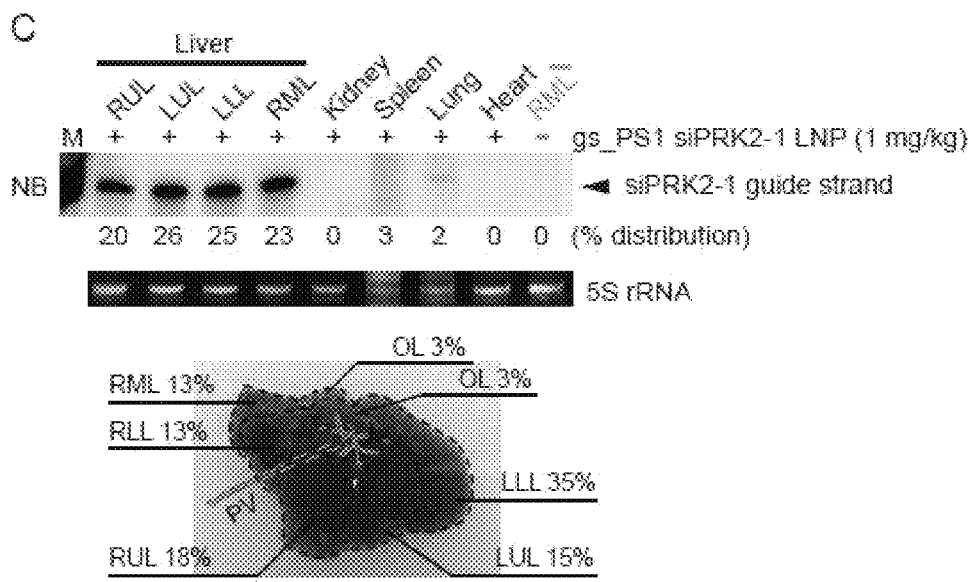

[FIG. 10D]
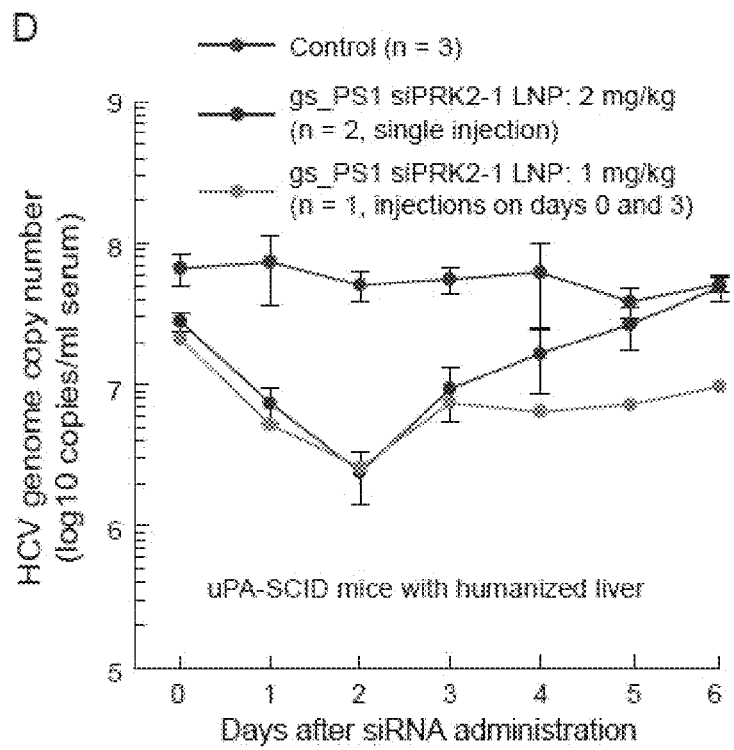
[FIG. 10E]
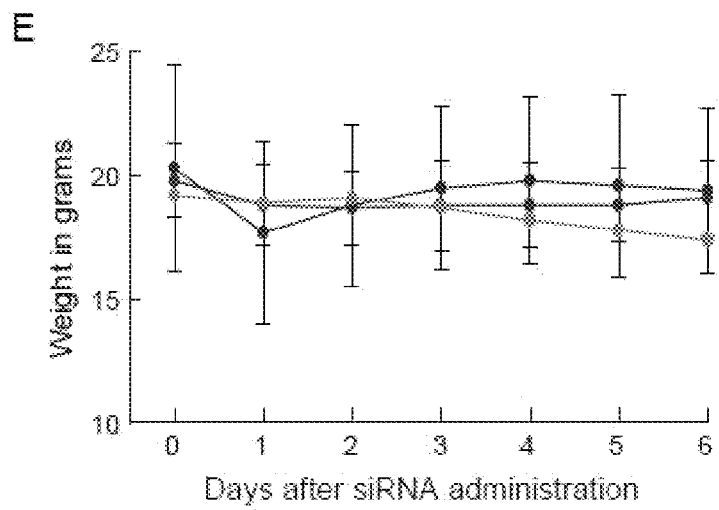

[FIG. 11A]
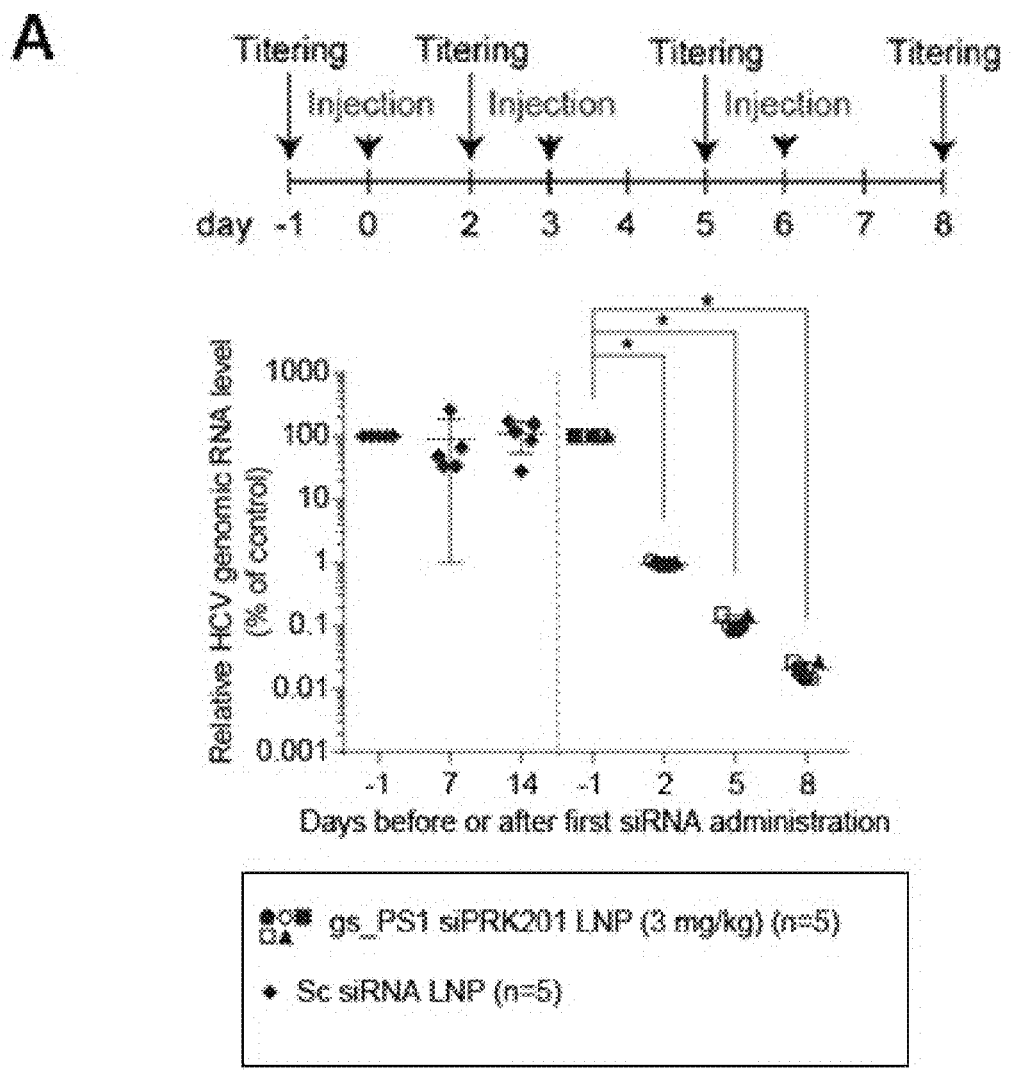

[FIG. 11B]
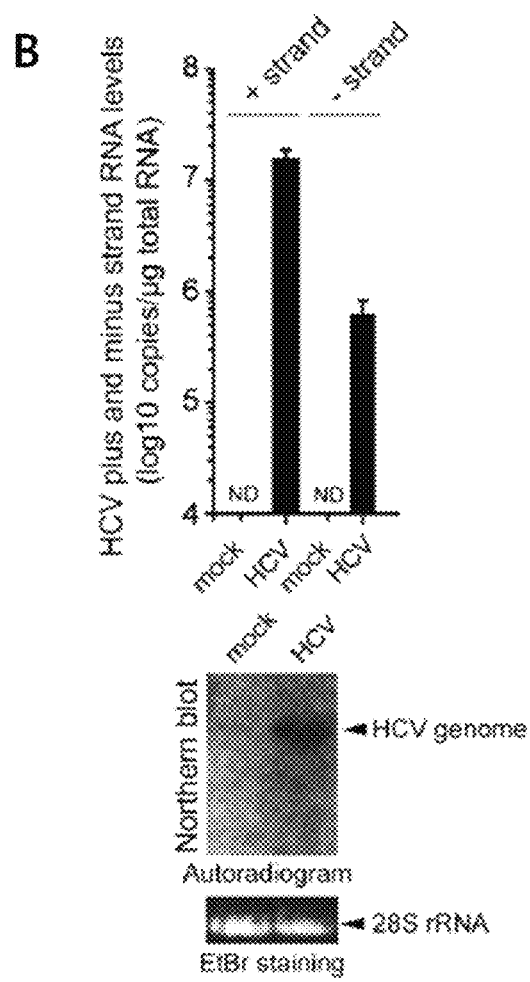

[FIG. 11C]
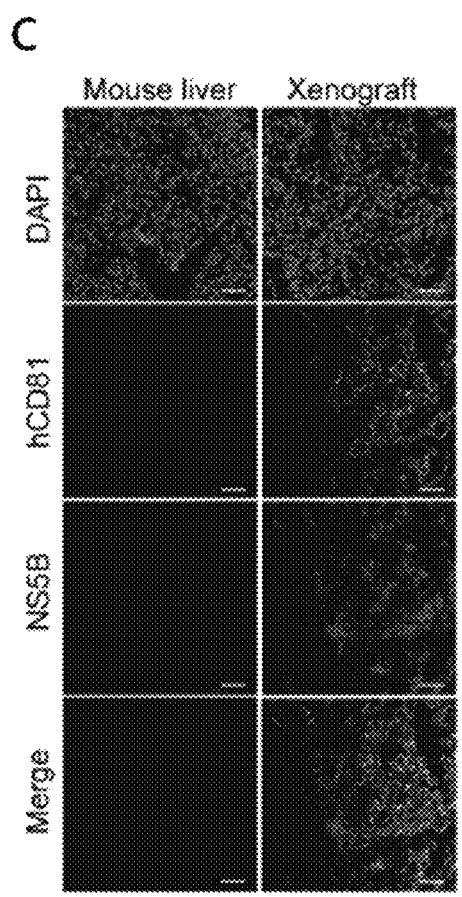

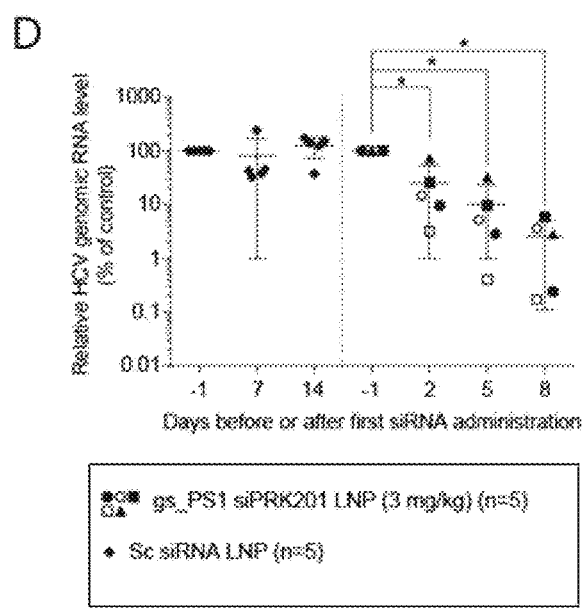
[FIG. 11D]

SIRNA TARGETING PRK2, WHICH IS HEPATITIS C VIRUS THERAPEUTIC AGENT

CROSS-REFERENCE TO RELATED APPLICATION

This application claims priority to and is a 35 U.S.C. §371 national phase application of PCT/KR2014/012561 (WO2015/093886), filed on Dec. 19, 2014 entitled "SIRNA TARGETING PRK2, WHICH IS HEPATITIS C VIRUS THERAPEUTIC AGENT", which application claims priority to and the benefit of Korean Patent Application No. 10-2013-0159000, filed Dec. 19, 2013; the disclosures of which is incorporated herein by reference in their entirety.

SEQUENCE STATEMENT

Incorporated by reference herein in its entirety is the Sequence Listing entitled "US15105516_amended_sequence_listing_ST25" created Feb. 24, 2017, size of 9 kilobyte.

TECHNICAL FIELD

The present invention relates to a composition for treating hepatitis C using a novel siRNA targeting PRK2.

BACKGROUND ART

Hepatitis C virus (HCV) is the major etiologic agent of non-A, non-B hepatitis. Currently, more than 170 million people worldwide are chronically infected with HCV. Persistent HCV infection causes chronic hepatitis that can lead to liver cirrhosis and hepatocellular carcinoma. A limited number of effective therapeutic agents specific to HCV are being currently used, but they are still used by combined administration of interferon used as a conventional standard therapeutic agent. The current standard of care for patients with chronic hepatitis C is pegylated interferon (hereinafter referred to as 'IFN') plus the nucleoside analogue ribavirin. However, IFN and ribavirin often lead to various side effects as administered alone or in combination, and the sustained virological response rate of IFN against certain HCV genotypes is less than 50%. Currently, only a few inhibitors of HCV enzymes including nonstructural protein (NS)3/NS4A protease and NS5B RNA-dependent RNA polymerase (RdRp), both of which are essential viral components of RNA replicase, are in clinical tests or have been approved for clinical applications. Development of HCV enzyme-specific therapeutics has been hampered because of rapid emergence of resistant mutants caused by the error-prone nature of the viral RdRp. Thus, in addition to viral enzyme targets, host targets have emerged as attractive options for anti-HCV drug development. RNA interference (RNAi) mediated by small interfering RNA (siRNA) is an effective, specific therapeutic entity to silence viral RNA genes. Several previous reports demonstrated the potential use of synthetic and vector-based siRNAs (short hairpin RNAs; shRNAs) as a therapy for HCV by directing siRNAs against various regions of the HCV genome.

However, besides the absence of improved delivery tools, rapid emergence of resistant mutants is a major obstacle in therapeutic application of siRNAs targeted to the viral genome. Because host target mRNAs have a lower chance of escaping from RNAi silencing, host factors required for HCV replication and propagation may be promising targets for anti-HCV siRNA therapy. We previously showed that HCV NS5B RdRp is phosphorylated by protein kinase C-related kinase 2 (PRK2), a Thr/Ser kinase belonging to the protein kinase C family HCV replication was shown to be positively regulated by PRK2 overexpression and is suppressed by pharmacological inhibition of PRK2 with the PRK2 inhibitors HA1077 and Y27632.

Despite recent progress, systemic delivery has been the major hurdle for development of safe and effective siRNA-based therapeutics. The antiviral efficacy of siRNAs used for silencing of various cellular factors required for HCV replication or propagation has not yet been evaluated in vivo in part due to the lack of efficient liver-targeting, more specifically hepatocyte-targeting, siRNA delivery agents, or possibly due to low stability of siRNAs and/or toxicity induced by silencing of critical host factors.

The present invention has been completed by developing an active PRK2 siRNA and assessing whether the PRK2-silencing siRNA can be used as an additional therapeutic option for HCV.

DISCLOSURE

Technical Problem

The present invention is directed to providing a siRNA therapeutic agent exhibiting an anti-HCV activity in vivo through silencing of a PRK2 gene of a host.

Technical Solution

To solve the above problems, one aspect of the present invention provides a double-stranded small interfering RNA (siRNA) which has 15 to 30 base pairs, targets a nucleotide sequence region of PRK2 mRNA set forth in SEQ ID NO: 1 and consists of a guide strand and a passenger strand. Here, the guide strand has a complementary sequence to a consecutive base sequence of at least 15 base pairs in the targeted base sequence.

Another aspect of the present invention provides an expression vector including the siRNA.

Still another aspect of the present invention provides a composition for treating hepatitis C, which includes the siRNA.

Still another aspect of the present invention provides a use of the siRNA to prepare a pharmaceutical composition for treating hepatitis C.

Yet another aspect of the present invention provides a method of treating hepatitis C, which includes administering a pharmaceutically effective amount of the siRNA to a subject in need thereof.

Advantageous Effects

The present invention provides an siRNA targeting a host PRK2 gene, which shows an anti-HCV activity. According to one embodiments of the present invention, the siRNA can be effectively used as a hepatitis C therapeutic agent since the systemic delivery of the siRNA into particularly in vivo hepatocytes is possible by a lipid formulation thereof.

DESCRIPTION OF DRAWINGS

FIG. 1 shows silencing of PRK2 which specifically inhibits HCV RNA replication in vitro and an effect thereof: FIG. 1A shows various target regions of a siRNA in a human PRK2 mRNA sequence; FIG. 1B shows a schematic view of HCV subgenomic replicon RNA (ΔC and Neo represent the genes coding an N-terminal part of an HCV core protein and a neomycin phosphotransferase, respectively, and an NS protein is a viral non-structural protein essential for HCV replication); FIG. 1C and FIG. 1D shows the values represented by the ratios of HCV subgenomic RNA titers to a mock-siRNA-treated control group after Huh7 cells harboring a HCV subgenomic replicon (R-1) is transfected with 10 nM (FIG. 1C), and increasing concentrations (FIG. 1D) of the indicated PRK2-specific siRNA, as measured by real-time qRT-PCR (three independent experiments with triplicate determinations are performed: *$p<0.01$); FIG. 1E shows the result of IFN-β promoter activity assays preformed in HEK293 cells transfected with 100 nM siPRK2-1 or 1 μg/ml poly(I:C) (the normalized luciferase activity (Fluc/Rluc) of mock-treated cells is defined as 100, and the data are represented by means±standard deviation (SD) of six measurements from two independent experiments; Rluc represents *Renilla* luciferase; Fluc represents firefly luciferase); FIG. 1F shows the results of cell cycle analysis performed in Huh7 cells treated with siRNAs (50 nM) or LY294002 (50 μM), a potent PI3K inhibitor inducing a G1 phase block that was used as a positive control; and FIG. 1G shows the evaluation results of HCV IRES-mediated translation levels in Huh7 cells transfected with siRNAs (50 nM) and a dual reporter vector (two luciferase reporter genes in the assay vector are indicated by boxes; the normalized luciferase activity (Fluc/Rluc) of mock-treated cells is defined as 100, and the data are obtained from one of two independent experiments performed in duplicate.

FIG. 2 shows the results obtained by evaluating the relation of silencing of PRK2 isoforms or other related kinases to the HCV replication: FIG. 2A shows the Western blot analysis results of PRK2 and HCV NS5B performed after 48 hours of transfection in Huh7 cells harboring a HCV subgenomic replicon (R-1) which have been transfected with PRK2-specific siRNA, that is, siPRK2-1 (10 nM) (immunoblotting using an anti-tubulin antibody is used in an internal loading control group), FIG. 2B and FIG. 2C show the results obtained by analyzing silencing effects of siRNAs targeting PRK1 or PRK3 by subjecting presented proteins to Western blot analysis after an experiment is performed in the same manner as in the method (FIG. 2A) except that the siRNA is used at a higher concentration (50 nM) to silence the PRK1 and the PRK3 (a level of PRK3 mRNA is quantified by real-time RT-PCR), and FIG. 2E shows the results obtained by transfecting R-1 cells with 50 nM siRNAs targeting either ROCK1 or ROCK2, measuring ROCK and NS5B proteins levels by a Western blot analysis (FIG. 2D), and measuring a HCV RNA level by real-time qRT-PCR.

FIG. 3 shows the results showing the specific interaction between HCV NS5B and PRK2: FIG. 3A shows an alignment of an amino acid sequence of peptides indicated in a phage binding to HCV NS5B and a homology region corresponding to a PRK isozyme (PRK2 has a sequence (NGRLVRRAI-C) highly homologous to a peptide sequence binding to the HCV NS5B; the same amino acids in the PRK2 and selected peptides are underlined), and FIG. 3B shows the results obtained from a Western blot analysis after immunoprecipiting an R-1 cell lysate with an anti-PRK2 or anti-PRK1 antibody, wherein Lane 1 represents 10% of the cell lysate input used for the co-immunoprecipitation experiments.

FIG. 4 shows the cytotoxicity results of siPRK2-1 in Huh7 cells transfected with an increasing concentration of siPRK2-1 (data represent as means±SD of values of triplicate determinations).

FIG. 5 shows whether the phosphorylation of HCV NS5B is important for HCV RNA replication: FIG. 5A Huh7 cells transfected with a plasmid expressing HCV NS5B are either left untreated or treated with scrambled siRNA or siPRK2-1 prior to metabolic labeling with [$^{32}$P]-orthophosphate. The labeled NS5B proteins were immunoprecipitated (IP), resolved by SDS-PAGE, and analyzed by autoradiography, and phosphorylated, radiolabeled NS5B signals were quantified using a PhosphorImager. Results represent as means±SD of three experiments. A representative autoradiogram is shown below the bar graph. FIG. 5B shows In vitro RdRp assays are performed using transiently expressed NS5B from Huh7 cells treated with the indicated siRNAs. Shown in the right panel are the results of Western blot analyses for the indicated proteins in cell lysates from siRNA-treated cells and the immunoprecipitated flag-epitope-tagged NS5B protein. RdRp assays were performed with the immunoprecipitated NS5B protein using a poly(A)/$U_{20}$ RNA template. FIG. 5C shows Northern blot analysis of total RNA retrieved from Huh7 cells transfected with the indicated HCV RNA transcripts at the indicated time points. The 28S rRNA, detected by ethidium bromide staining, was used as a loading control. An in vitro-transcribed HCV RNA genome was used as the assay standard.

FIG. 6 shows in vitro and in vivo silencing potency of siPRK2-1 delivered by lipidoid ND98: FIG. 6A shows a chemical structure of the lipidoid ND98 (prepared by conjugate addition of an amine (a central connection region) to an acrylamide (upper and lower regions)), FIG. 6B shows a HCV genome titer quantified as shown in FIG. 1C after R-1 cells are transfected with 10 nM siPRK2-1 or scrambled siRNA using the indicated transfection reagents, and FIG. 6C shows the results obtained by injecting siPRK2-1 lipidoid nanoparticles (LNP) to BALB/c mice (five mice per group) at a dose of 1 mg/kg body weight and analyzing hepatocyte PRK2 mRNA level using qRT-PCR. Here, the PRK2 mRNA level is normalized to GAPDH, and the data are represented by representative values obtained from two independent experiments (*$p<0.05$).

FIG. 7 shows anti-HCV activities of siPRK2-1 LNPs in mouse xenograft models in which infectious HCV particles are produced: FIG. 7A shows HCV genome titers measured in sera of xenograft mice, which carry non-transfected Huh7 (Huh7/mock) or Huh7 transfected with HCV (genotype 2a, JFH1) in vitro transcript RNA genome (Huh7/HCV) by electroporation, on day 7 and 14 post-xenografting, using real-time qRT-PCR, FIG. 7B shows HCV plus- and minus-strand RNA copy numbers in the xenograft tissue, retrieved 4 weeks post-xenografting (ND: not detected), FIG. 7C shows the haematoxylin and eosin (H&E) staining and HCV core antigen immunohistochemical analysis of xenografts (4 weeks post-xenografting) (H&E; 4',6'-diaamidino-2-phenylindole (DAPI), nuclear staining; scale bar: 50 μm), FIG. 7D, FIG. 7E and FIG. 7F show serum HCV titers monitored at the indicated time points following drug administration or siRNA injection, that is, serum HCV genome titers in xenograft mice (three mice per group) retrieved after a single direct injection of HA1077 (25 mg/kg) as a PRK2 inhibitor into tumor (FIG. 7D) or intravenous injection (hereinafter referred to as 'i.v. injection') of siPRK2-1 or scrambled siRNA encapsulated into LNP at a dose of 1 mg/kg body weight (FIG. 7E) (chemically modified siPRK2-1(PS1_siPRK2-1) in (FIG. 7F) is administered in the same manner as in (E); *p<0.01; **p<0.05).

FIG. 8 shows that siPRK2-1/lipidoid or siPRK2-1 lipidoid nanoparticles do not induce the production of IFN-α and TNF-α in hPBMCs: FIG. 8A to FIG. 8D show the results obtained by transfecting the hPBMCs with 10 nM siPRK2-1 or scrambled siRNA(Sc) or 1 µg/well of poly(I:C) using lipidoid ND98 or lipidoid nanoparticles (LNP), optionally directly adding 50 µg/ml of poly(I:C) to the culture medium to stimulate the cells and then measuring IFN-α (FIG. 8A and FIG. 8C) and TNF-α (FIG. 8B and FIG. 8D) secreted from the stimulated cells. Here, the results represent the data obtained from one of two independent experiments with similar results.

FIG. 9 shows anti-HCV activities of chemically modified siPRK2-1 derivatives in HCV-infected cells: FIG. 9A shows the results of evaluation of serum stability of non-modified siPRK2-1 (2 µM) in 45% human plasma (siRNA is incubated for the indicated time period, RNA extracted from each sample is resolved by electrophoresis on a denaturing 15% polyacrylamide gel, siPRK2-1 guide strands (indicated by arrows) are detected using a Northern blot analysis, and the relative signal intensity is plotted using SigmaPlot to estimate the siPRK2-1 guide strands half-life; the data are obtained from one representative experiment of two independent experiments with similar results), FIG. 9B shows the results obtained by evaluating the stability of chemically modified PRK2 siRNAs in human plasma as described in (FIG. 9A), and (FIG. 9C) and (FIG. 9D) shows anti-HCV activities of selected modified PRK2-1 siRNAs as evaluated in HCV (genotype 2a, JFH1)-infected Huh7 cells (the cells are infected with HCV (multiplicity of infection: 0.25) for 4 hours, remain untreated (Ctrl), or transfected with siRNAs targeting PRK2 or scrambled siRNA(Sc) (10 nM) using lipofectamine RNAiMAX, washed after 4 hours, and incubated in fresh, complete medium for another 48 hours (FIG. 9D), and the Huh7 cells are optionally transfected with siRNAs (10 nM) in advance, washed after 4 hours, infected with HCV for 4 hours, and then incubated in fresh, complete medium for another 48 hours to perform quantification (FIG. 9D); the copy number of the HCV genome is measured using qRT-PCR, and three independent experiments measured in triplicate were performed: *p<0.01).

FIG. 10 shows a long-term silencing effect of the anti-HCV activities of siPRK2-1 and gs_PS1 siPRK2-1: FIG. 10A and FIG. 10B show levels of siPRK2-1 guide strands (FIG. 10A) and PRK2 mRNAs (FIG. 10B) at day 3, 6 and 9 in primary mouse hepatocytes transfected with 10 nM non-modified siPRK2-1, PS-modified siPRK2-1 (gs_PS1), or scrambled control group siRNA(Sc) (using lipidoid ND98), FIG. 10C shows the results obtained by i.v. injecting gs_PS1 siPRK2-1 LNPs at a dose of 1 mg/kg and analyzing a level of the siPRK2-1 guide strands in each organ and four other liver lobes, and schematically shows liver samples used to extract the total RNAs (each liver lobe is represented by units of % by weight) in a lower panel (the total RNAs obtained from a total RNAs of a control group mouse (Last lane) are included as the control group, a 5S rRNA band is visualized through ethidium bromide staining to prove the equivalent loading of RNA, and the data represent representative of two independent experiments with similar results; RUL: right upper lobe; LUL: left upper lobe; LLL: left lower lobe; RML: right middle lobe; RLL: right lower lobe; OL: omental lobe; and PV: portal vein), and FIG. 10D and FIG. 10E show changes in serum HCV RNA titers (FIG. 10D) and body weights of severe chimeric combined immunodeficiency (SCID) mice (uPA/SCID) having humanized livers during an experiment by infecting the chimeric mice with HCV (genotype 1b) and then i.v. injecting gs_PS1 siPRK2-1 LNP or PBS into the chimeric mice.

FIG. 11 shows an anti-HCV effect of gs_PS1 siPRK2-1 LNP in a xenograft mouse model: FIG. 11A shows relative serum HCV RNA titers from NOD/SCID mice subcutaneously xenografted with HCV-replicating Huh7 cells are monitored at the indicated time points before and after consecutive i.v. injections of 3 mg/kg of Sc siRNA LNP or gs_PS1 siPRK2-1 LNP (five mice per groups) every three days. The data indicated by different symbols differently represent an individual mouse (*p<0.01). FIG. 11B shows HCV (+) and (−) strand RNA copy numbers from the xenograft tissues retrieved 4 weeks post-xenografting of HCV-infected Huh7 cells into NOD/SCID mice livers. Here, ND represents 'not detected.' Northern blot analysis of the HCV genome in the transplanted tissues is shown in a lower panel. 28S rRNA detected by ethidium bromide staining is used as a loading control. FIG. 11C shows the results of detecting HCV NS5B and human CD81 (hCD81) in liver xenografts retrieved 4 weeks post-xenografting using an immunohistochemical analysis. DAPI represents a nuclear stain, and a scale bar is indicated by 100 µm. FIG. 11D shows anti-HCV effects of Sc siRNA or gs_PS1 siPRK2-1 (3 mg/kg) encapsulated into LMP in the orthotopic xenograft model as described in (FIG. 11B) and (FIG. 11C). Here, the indicated siRNA LNP is i.v. injected three times into the mice every three days, and the data represent relative serum HCV RNA titers (*p<0.01).

BEST MODE

Hereinafter, the configurations of the present invention will be described in detail.

The present invention provides a double-stranded small interfering RNA (siRNA) which has 15 to 30 base pairs, targets a nucleotide sequence region of PRK2 mRNA set forth in SEQ ID NO: 1, and consists of a guide strand and a passenger strand. Here, the guide strand has a complementary sequence to a consecutive base sequence of at least 15 base pairs in the targeted base sequence.

The present invention is related to a technology of inhibiting the expression of PRK2 mRNA in mammals including human, or an alternative splice form or mutant form thereof, or the same family of PRK2 genes. This may be achieved by administering the indicated dose of the siRNA provided in the present invention to patients to reduce a level of target mRNA.

The PRK2 may be PRK2 and mutants thereof derived from a mammal, preferably human, or the same family as human. The same family as the human refers to another mammal whose gene or mRNA has a sequence homology of 80% with respect to a human PRK2 gene or mRNA transcribed therefrom and specifically may include human, primates, rodents, etc. According to one embodiment, a cDNA sequence of a sense strand corresponding to mRNA coding for PRK2 may be set forth in SEQ ID NO: 1. More particularly, the siRNA according to one embodiment of the present invention targets a $527^{th}$ to $545^{th}$ nucleotide sequence inside human PRK2 mRNA, and SEQ ID NO: 1 refers to this region. This target region is conserved in mouse mRNA, and thus the siRNA may target this region.

The term 'target mRNA' used herein refers to human PRK2 mRNA, a PRK2 mRNA derived from the same family as human, or a mutant or alternative splice structure thereof. Specifically, the target mRNA may be NM_006256, NM_178654, etc. Therefore, the siRNA according to one embodiment of the present invention may target the PRK2 mRNA derived from human or the same family as human, or an alternative splice form or mutant form thereof.

In this specification, the expression 'targeting an mRNA region' means that the siRNA has partial or full-length of a base sequence of the mRNA region, for example, has a base sequence complementary to 85 to 100% of the base sequence of the mRNA region, and thus may specifically bind to the mRNA.

In this specification, the term 'complementary' means that both strands of a polynucleotide may form base pairs. Both strands of a complementary polynucleotide form base pairs in Watson-Crick model, thereby forming a duplex. Unless otherwise indicated in the present invention, a base U may be substituted with a base T.

The siRNA according to one embodiment of the present invention serves to induce PRK2 mRNA destruction through an RNAi mechanism and thus prevent or reduce the expression of the PRK2 protein. The siRNA refers to a small inhibitory RNA duplex that triggers RNA interference (RNAi) pathway. Specifically, the siRNA is dsRNA including a sense RNA strand and an antisense strand complementary to the sense RNA strand. Here, both strands consist of 15 to 30 base pairs, particularly 19 to 25 base pairs, and more particularly 19 to 21 base pairs. The siRNA includes a duplex region and has a structure in which a single strand forms a hairpin or stem-loop structure or may be a duplex of two separate strands. A passenger RNA strand has the same sequence as a nucleotide sequence of an mRNA sequence of a target gene. In this case, the passenger RNA strand and a passenger RNA strand complementary to the passenger strand may form a duplex by means of Watson-Crick complementary base pairing. The guide strand of the siRNA is collected into an RNA-induced silencing complex (RISC) so that the RISC senses a target mRNA complementary to the guide strand and then induce inhibition of cleavage and translation of the target mRNA.

According to one embodiment, the siRNA includes a passenger strand and a guide strand. In this case, the passenger strand and the guide strand forms a duplex consisting of 15 to 30 base pairs and the duplex may have a symmetric structure having blunt ends without unpaired overhanging or an asymmetric structure having a unpaired overhanging consisting of at least 1 to 5 nucleotides. The unpaired overhanging nucleotides may have any sequence but may have a sequence to which two deoxythymidines (dTs) are bound.

The guide strand is hybridized with the target region of the mRNA of SEQ ID NO: 1 under a physiological condition. The description 'hybridized under physiological condition' means that a guide strand of the siRNA is in vivo hybridized with a specific target region of mRNA. Specifically, the guide strand may have 85% or more sequence complementarity to the target mRNA region, preferably a base sequence of SEQ ID NO: 1. More particularly, the guide strand may have a sequence completely complementary to at least consecutive 15 base pairs, preferably at least consecutive 18 base pairs in the base sequence of SEQ ID NO: 1.

According to a preferred embodiment, the siRNA may consist of a guide strand sequence set forth in SEQ ID NO: 2, and a passenger strand sequence set forth in SEQ ID NO: 3.

The siRNA may have a naturally occurring non-modified ribonucleic acids unit structure, or it may be chemically modified, and for example, it may be synthesized such that the sugar or base structure of at least one ribonucleic acid, a bond between ribonucleic acids may have at least one chemical modification. Through the chemical modification of siRNA desirable effects such as improved resistance to nuclease, increased intracellular uptake, increased cell targeting (target specificity), increased stability, or decreased off-target effect such as decreased interferon activity, immune response and sense effect, and the like may be obtained without influencing the original RNAi activity. The chemical modification method of siRNA is not specifically limited, and one of ordinary skills in the art may synthesize and modify the siRNA as desired by a method known in the art (Andreas Henschel, Frank Buchholz 1 and Bianca Habermann (2004) DEQOR: a web based tool for the design and quality control of siRNAs. Nucleic Acids Research 32(Web Server Issue): W113-W120). For example, a phosphodiester bond of siRNA sense or antisense strand may be substituted with boranophosphate or phosphorothioate to increase resistance to nucleic acid degradation. For example, it may be introduced at 3' or 5' end or both ends of siRNA sense or antisense strand, preferably only at RNA terminus, for example, 3' end overhang (for example, (dT)n, n=an integer of 1-5, preferably of 2-4). For another example, ENA (Ethylene bridge nucleic acid) or LNA (Locked nucleic acid) may be introduced at 5' or 3' end, or both ends of siRNA sense or antisense strand, and preferably, it may be introduced at 5' end of siRNA sense strand. Thereby, siRNA stability may be increased, and an immune response and non-specific inhibition may be reduced, without influencing the RNAi activity. For yet another example, a 2'-OH group of ribose ring may be substituted with —NH$_2$ (amino group), —C-allyl (allyl group), —F (fluoro group), or —O-Me (or CH$_3$, methyl group). For example, 2'-OH group of ribose of 1st and 2nd nucleic acids of antisense strand may be substituted with 2'-O-Me, 2'-OH groups of ribose of $2^{nd}$ nucleic acid of antisense strand may be substituted with 2'-O-Me, or 2'-OH of ribose of guanine (G) or uridine (U) containing nucleotides may be substituted with 2'-O-Me (methyl group) or 2'-F (fluoro group).

In addition to the above described chemical modifications, various chemical modifications may be made, and only one chemical modification may be made or a plurality of chemical modifications may be made in combination.

In the chemical modification, it is preferable that the activity of knockdown of gene expression may not be reduced while stabilizing the double stranded structure of the siRNA, and thus, minimum modification may be preferred.

According to a preferred embodiment, the chemically modified siRNA may be an siRNA consisting of a guide strand sequence set forth in SEQ ID NO: 4 or 5 and a passenger strand sequence set forth in SEQ ID NO: 3, 9 or 10.

According to one embodiment, the chemically modified siRNA exhibits improved stability compared to non-modified siRNAs. And, a ligand such as cholesterol, biotin, or cell penetrating peptide may be attached at 5'- or 3'-end of siRNA.

The siRNA of the present invention may be manufactured by chemical synthesis or in vitro transcription, or by cleaving long double stranded RNA with dicer or other nuclease having similar activities. Alternatively, as described above, siRNA may be expressed through plasmid or a viral expression vector such as an adeno-associated virus, a retrovirus, a vaccinia virus, an oncolytic adenovirus, and the like.

Accordingly, the present invention provides an expression vector including the siRNA.

The siRNA includes ribonucleic acid sequence itself, and a recombinant vector (expression vector) expressing the same.

A candidate siRNA sequence may be selected by experimentally confirming whether or not a specific siRNA sequence induces interferon in human peripheral blood mononuclear cells (PBMC) comprising dendritic cells, and then, selecting sequences which do not induce an immune response.

Hereinafter, a drug delivery system (DDS) for delivering the siRNA will be described.

A nucleic acid delivery system may be used to increase an intracellular delivery efficiency of siRNA.

The nucleic acid delivery system for delivering nucleic acid material into cells may include a viral vector, a non-viral vector, liposome, cationic polymer micelle, emulsion, solid lipid nanoparticles, and the like. The non-viral vector may have high delivery efficiency and long retention time. The viral vector may include a retroviral vector, an adenoviral vector, a vaccinia virus vector, an adeno-associated viral vector, an oncolytic adenovirus vector, and the like. The nonviral vector may include plasmid. In addition, various forms such as liposome, cationic polymer micelle, emulsion, solid lipid nanoparticles, and the like may be used. The cationic polymer for delivering nucleic acid may include natural polymer such as chitosan, atelocollagen, cationic polypeptide, and the like and synthetic polymer such as poly(L-lysine), linear or branched polyethylene imine (PEI), cyclodextrin-based polycation, dendrimer, and the like.

The lipid nanoparticles form nucleic acid-lipid particles with the siRNA. The nucleic acid-lipid particles generally include a cationic lipid, a non-cationic lipid, a sterol, and a lipid for preventing coagulation of particles (for example, a PEG-lipid conjugate). The nucleic acid-lipid particles have an extended cycle lifespan after they are i.v. injected and are accumulated at a remote position (for example, a position physically remote from an administration site) and thus extremely beneficial for a systemic application. Also, when nucleic acids are present in the nucleic acid-lipid particles according to one embodiment of the present invention, the nucleic acids are resistant to destruction by nucleases in an aqueous solution. The nucleic acid-lipid particles and a method of preparing the same are, for example, disclosed in U.S. Pat. Nos. 5,976,567; 5,981,501; 6,534,484; 6,586,410; and 6,815,432; and WO 96/40964.

The nucleic acid-lipid particles may also include one or more additional lipids and/or other components, for example, cholesterol. The other lipids may be included in a liposome composition for various purposes, for example, a purpose of preventing oxidation of lipids or attaching a ligand onto a surface of a liposome. Any number of lipids may exist since the liposome composition may include amphipathic, neutral, cationic, and anionic lipids. Such lipids may be used alone or in combination.

The additional components that may be present in the nucleic acid-lipid particles include a bilayer stabilizing component, for example, a polyamide oligomer (for example, see U.S. Pat. No. 6,320,017), a peptide, a protein, a detergent, and lipid derivatives, for example, PEG conjugated to phosphatidylethanolamine, and PEG conjugated to ceramide (see U.S. Pat. No. 5,885,613). The nucleic acid-lipid particles may include at least one second aminolipid or cationic lipid, a neutral lipid, a sterol, and a lipid selected to reduce aggregation of lipid particles during formation in order to contribute to structural stabilization of particles which prevent charge-induced aggregation during the formation.

The nucleic acid-lipid particles may be prepared using an extrusion method or an in-line mixing method. The extrusion method (also referred to as a batch process) is a method of preparing a void liposome (e.g., having no nucleic acids) in advance and adding nucleic acids to the void liposome, which is disclosed in U.S. Pat. Nos. 5,008,050; 4,927,637; and 4,737,323; and *Biochim Biophys Acta.* 1979 Oct. 19; 557(1):9-23; *Biochim Biophys Acta.* 1980 Oct. 2; 601(3): 559-7; *Biochim Biophys Acta.* 1986 Jun. 13; 858(1): 161-8; and *Biochim. Biophys. Acta* 1985 812, 55-65, the disclosures of which are incorporated herein by reference.

The in-line mixing method is a method of adding lipids and nucleic acids to a mixing chamber side by side. The mixing chamber may be simply a T-connector, or any of other mixing chambers known in the related art. Such methods are disclosed in U.S. Pat. Nos. 6,534,018 and 6,855,277; US Patent Publication No 2007-0042031, and *Pharmaceuticals Research*, Vol. 22, No. 3, March 2005, pp. 362-372, the disclosures of which are incorporated herein by reference.

A formulation of the present invention may be prepared using any methods known in the related art.

According to one embodiment, the nucleic acid-lipid particles may be synthesized using a lipidoid ND98 (MW 1487) (see FIG. 6A), cholesterol, and PEG-ceramide C16: 133 mg/ml of lipidoid ND98; 25 mg/ml of cholesterol, and 100 mg/ml of PEG-ceramide C16. A stock solution of ND98, cholesterol and PEG-ceramide C16 may, for example, be mixed at a molar ratio of 42:48:10. A combined lipid solution may be mixed with aqueous siRNA (for example, in sodium acetate, pH 5) so that a final concentration of ethanol is in a range of about 35 to 45% and a final concentration of sodium acetate is in a range of about 100 to 300 mM. Generally, the lipid-siRNA nanoparticles may be spontaneously formed during mixing. Depending on a desired particles size distribution, the resulting nanoparticles mixture may be extruded through a polycarbonate membrane (for example, having a cut-off size of 100 nm), for example, using a thermobarrel extruder such as Lipex Extruder (Northern Lipid, Inc). In some cases, an extrusion process may be omitted. Ethanol removal and simultaneous buffer exchange may be carried out by a method such as dialysis or tangential flow filtration. A buffer may be exchanged with phosphate-buffered saline (PBS) at about pH 7, for example, about pH 6.9, about pH, about pH 7.1, about pH 7.2, about pH 7.3, or about pH 7.4.

The siRNA may be introduced into cells in vivo or in vitro in the form of a complex with a nucleic acid delivery system.

According to one embodiment, the silencing of PRK2 by the siRNA of the present invention may remarkably reduce a HCV genome titer in HCV-replicating cells, and an antiviral effect interferes with cell cycles and a translation procedure by means of HCV IRES or does not induce IFN-α or TNF-α. Also, the liver-specific delivery of the siRNA remarkably reduces a level of PRK2 mRNA in hepatocytes.

Accordingly, the siRNA according to one embodiment of the present invention may be used as a hepatitis C therapeutic agent, and thus the present invention provides a composition for treating hepatitis C including the siRNA.

The present invention also provides a use of the siRNA to prepare a pharmaceutical composition for treating hepatitis C.

The pharmaceutical composition according to one embodiment of the present invention may further include at least one anti-HCV agent for combined administration selected from the group consisting:

1) at least one HCV non-structural protein inhibitor selected from the group consisting of NS2, NS3, NS4A, NS4B, NS5A, and NS5B;

2) at least one HCV structural protein inhibitor selected from the group consisting of capsid protein C, an envelope glucoprotein E1 or E2, and a p7 protein;

3) at least one broad-spectrum anti-viral agent selected from the group consisting of IFN-α and ribavirin;

4) an HCV gene inhibitor such as a HCV internal ribosome entry site (IRES), a capsid protein C-coding gene, a HCV 3'-untranslated region (3'-UTR), or commonly conserved regions of sequences in various HCV genotypes (an HCV gene and a conserved region of a sequence on a complementary gene thereof); and 5) a host target gene inhibitor for controlling the replication or proliferation of HCV such as a full-length PRK2 gene, host factors Hsp90 and PDK1 for regulating functions of PRK2, a factor participating in the entry of HCV (including CD81), or a host factor binding to a HCV structural or non-structural protein to regulate the replication or regulate interaction between HCV structural proteins, or binding to a HCV structural protein to regulate the functions.

The gene inhibitor may be an inhibitor that functions to inhibit the expression of a gene. In this case, the gene inhibitor may be a peptide, a nucleic acid or a compound that bind to the gene. For example, the inhibitor may be an antisense-oligonucleotide against the gene, siRNA, shRNA, miRNA, or a vector including the same. Such an antisense-oligonucleotide, siRNA, shRNA, miRNA or a vector including the same may be constructed using methods known in the related art.

The antisense-oligonucleotide, siRNA, shRNA, miRNA or a vector including the same may have a complementary sequence to entire or partial mRNA sequence transcribed from a target gene or fragments thereof and bind to the mRNA to inhibit the target gene or fragments thereof.

The protein inhibitor may be a target-specific antibody. A polyclonal antibody, a monoclonal antibody, a human antibody, a humanized antibody, or antibody fragments may be used as the antibody.

The pharmaceutical composition according to one embodiment of the present invention includes a pharmaceutically acceptable carrier, that is, a carrier commonly used in a field of medicine, and a vehicle. Specifically, the pharmaceutical composition includes an ion exchange resin, alumina, aluminum stearate, lecithin, a serum protein (e.g., human serum albumin), a buffer material (e.g., various phosphates, glycine, sorbic acid, potassium sorbate, a partial glyceride mixture of saturated vegetable fatty acids, etc.), water, a salt or electrolyte (e.g., protamine sulfate, disodium hydrogen phosphate, potassium monohydregen phosphate, sodium chloride and a zinc salt), colloidal silica, magnesium trisilicate, polyvinyl pyrrolidone, a cellulose-based substrate, polyethylene glycol, sodium carboxymethyl cellulose, polyarylate, wax, polyethylene glycol, or a wool fat, but the present invention is not limited thereto. Also, a contrast medium composition according to one embodiment of the present invention may further include a lubricant, a wetting agent, an emulsifying agent, a suspending agent, or a preservative, etc in addition to the above-described components.

Also, the pharmaceutical composition according to one embodiment of the present invention may be prepared into an aqueous solution for parenteral administration. Preferably a Hank's solution, a Ringer's solution, or a buffer solution such as physically buffered saline may be used. A substrate that can enhance a viscosity of a suspension, such as sodium carboxymethyl cellulose, sorbitol or dextran, may be added to an aqueous injectable suspension.

In addition, the pharmaceutical composition according to one embodiment of the present invention may be in the form of a sterile injectable preparation of a sterile aqueous or oily suspension for injection. Such a suspension may be formulated using a proper dispersing agent or wetting agent (for example, Tween 80) and a suspending agent according to the techniques known in the related art.

Additionally, the sterile injectable preparation may be a sterile injectable solution or suspension (for example, a solution in 1,3-butanediol) in a non-toxic parenterally usable diluent or solvent. The vehicle and solvent that may be used may include mannitol, water, a Ringer's solution, and an isotonic sodium chloride solution. Also, sterile non-volatile oil is generally used as a solvent or a suspending medium. Any oil including synthetic mono- or di-glycerides may be used as long as the oil is of low pungency and non-volatile.

Another aspect of the present invention is related to the use of the siRNA according to one embodiment of the present invention in connection with treatments and/or prevention of disease conditions. Examples of diseases that may be treated according to the method of the present invention may include hepatitis C as described above.

Accordingly, still another aspect of the present invention provides a method of treating hepatitis C, which includes administering a pharmaceutically effective amount of the siRNA to a subject in need thereof. Here, the administration of the siRNA may inhibit, stop, delay or prevent the occurrence or progression of the disease conditions.

A human being, a dog, a monkey, a cat, a rodent, for example, a mouse or rat may be used as the subject without limitation.

The term "effective amount" refers to an amount required to delay or completely stop the occurrence or progression of a certain disease to be treated. Such an amount may vary according to the health and physical state of a subject to be treated, a taxonomic group of subjects to be treated, a desired level of protection, evaluation of medical situations, and other related factors, for example, types of siRNAs, types of formulations, age, weight, general health conditions, gender and diet of a patient, an administration time, a route of administration, a treatment period, a combined administration agent, etc. Such an amount may be in a relatively wide range that may be measured through conventional attempts. To minimize undesirable side effects such as immune responses while achieving a significant effect in inhibiting PRK2, for example, a concentration of the siRNA in a composition or a concentration of the siRNA used or for treatment may be in a range of 0.001 to 1000 nM, preferably 0.01 to 100 nM, and more preferably 0.1 to 10 nM, but the present invention is not limited thereto.

MODE FOR INVENTION

These and other advantages and features of the present invention and method of achieving them will be apparent from the following description of preferred embodiments. However, the present invention is not limited to the following embodiments but will be embodied in various forms. That is, the embodiments of the present invention play a role of making the disclosure of the present invention complete and are provided to inform a person who has an ordinary knowledge and skill in the art to which this invention belongs of the scope of the invention. This invention should be defined based on the scope of claims.

<Example 1> SiRNA Preparation and Experimental Method (Cell Line and Culture)

A human hepatocellular carcinoma cell line Huh7 was cultured in a Dulbecco's modified Eagle's medium (DMEM) supplemented with 10% fetal bovine serum, 2 mM L-glutamine, 100 U/ml of penicillin, 100 µg/ml of streptomycin and 0.1 mM non-essential amino acids under the standard culture conditions (5% $CO_2$, 37° C.). Huh7 cells harbored with HCV subgenomic replicon RNA (R-1 cell line) were maintained in a complete DMEM supplemented with 1 mg/ml of G418. Human embryonic kidney (HEK) 293 cells were cultured in DMEM including 10% FBS, 100 U/ml of penicillin, 100 µg/ml of streptomycin and 1 mM sodium pyruvate.

(Plasmids)

A bicistronic dual luciferase vector with a cap-dependent Renilla luciferase reporter (RLuc) translation site and an HCV internal ribosome entry site (IRES)-mediated firefly luciferase (FLuc) translation site is disclosed in an article by Kim M G, et al. (*Biochem. Biophys. Res. Commun.* 2012, vol. 421, pp. 112-118). A plasmid JFH1 used to produce infectious HCV particles was kindly provided by Dr. Takaji Wakita (National Institute of Infectious Diseases, Japan).

(Antibodies and Reagents)

The following antibodies were obtained: a rabbit polyclonal anti-PRK2 antibody (Cell Signaling Technology, Danvers, Mass., USA), mouse monoclonal anti-Rho-associated kinase (ROCK)1(4H247) and ROCK2(30-J) antibodies (Santa Cruz Biotechnology, Santa Cruz, Calif., USA), a mice monoclonal anti-PRK1 antibody (clone 49/PRK1, BD Biosciences, San Jose, Calif., USA) and an anti-α-tubulin antibody (Calbiochem, La Jolla, Calif., USA). The rabbit polyclonal anti-NS5B antibody was produced in the present inventor's laboratory. Polyinosinic:polycytidylic acid (poly (I:C)) that was a double-stranded RNA analogue was obtained from Sigma-Aldrich (St. Louis, Mo., USA). HCV 3'-UTR RNA was prepared through an in vitro transcription.

(siRNAs)

siRNAs targeting human PRK1, PRK2, PRK3, ROCK1 or ROCK2 were designed according to mRNA sequence obtained from GenBank (NM 213560, 006256, 013355, 005406, and 004850, respectively), and obtained from ST Pharm (Seoul, Korea). A siRNA region targeting PRK2 mRNA is shown in FIG. 1A.

Guide strands of other siRNAs used to silence other PRK isoforms are as follows:

```
1) PRK1:
siPRK1-1
(5'-GAUGAUGUCAAUCUUGGUCTT-3': SEQ ID NO: 11);
and siPRK1-2
(5'-GCUGUAGGUCUGGAUCAUGTT-3': SEQ ID NO: 12);
2) PRK2:
siPRK2-1
(5'-UUUUCAGCUCCUUCUUUGAUU- 3': SEQ ID NO: 2);

3) PRK3:
siPRK3-1
(5'-AAGCAGUUUCACCACGUUCTT-3': SEQ ID NO: 13);
and
```

```
siPRK3-2
(5'-CUCCUGCUUCUUCAGUGCUTT-3': SEQ ID NO: 14).
```

SiRNAs used to silence ROCK1 and ROCK2 are as follows:

```
1) ROCK1:
siROCK1-1
(5'-GCAGCAGGUUGUCCAUUUUTT-3': SEQ ID NO: 15);
and siROCK1-2
(5'-GCAAACAAUCCGAAUUCACTT-3': SEQ ID NO: 16);

2) ROCK2:
siROCK2-1
(5'-UCCCCGCCCCUCAGUCAGATT-3': SEQ ID NO: 17);
and siROCK2-2
(5'-GCCUGCCUCUAGCUCCGGCTT-3': SEQ ID NO: 18).
```

A scrambled siRNA consists of the following duplex sequences:

```
                                        (SEQ ID NO: 19)
    5'-GUUCAGCGUGUCCGGCGAGUU-3';
and (SEQ ID NO: 20)
    5'-CUCGCCGGACACGCUGAACUU-3'
```

A 2'-OH group present on the backbone per ribose was substituted with a 2'-O-methyl group (2'-O-Me) or 2'-fluoro group (2'-F) to modify siPRK2-1. Also, modification was introduced by replacing one non-bridging oxygen atom on the backbone phosphate between two ribonucleotides with a sulfur atom to create a phosphorothioate (PS) linkage. The chemically modified siPRK2-1 derivatives are listed in the following Table 1.

TABLE 1

| siRNA | Sequences and modified residues |
|---|---|
| siPRK2-1 (non-modified) | 5'-UCAAAGAAGGAGCUGAAAAUU-3'<br>(SEQ ID NO: 3)<br>3'-UUAGUUUCUUCCUCGACUUUU-5'<br>(SEQ ID NO: 2) |
| ps_2'-O-Me | 5'-UCAAAGAAGGAGCUGAAAAUU-3'<br>(SEQ ID NO: 6) |
| gs_All-F | 3'-UUAGUUUCUUCCUCGACUUUU-5'<br>((SEQ ID NO: 7) |
| gs_Py-F | 3'-UUAGUUUCUUCCUCGACUUUU-5'<br>(SEQ ID NO: 8) |
| ps_PS1 | 5'-UCAAAGAAGGAGCUGAAAsAUU-3'<br>(SEQ ID NO: 9) |
| ps_PS2 | 5'-UCAAAGAAGGAGCUGAAsAsAUU-3'<br>(SEQ ID NO: 10) |
| gs_PS1 | 3'-UUAsGUUUCUUCCUCGACUUUU-5'<br>(SEQ ID NO: 4) |
| gs_PS2 | 3'-UUAsGsUUUCUUCCUCGACUUUU-5'<br>(SEQ ID NO: 5) |
| ps_PS1/gs_PS1 | 5'-UCAAAGAAGGAGCUGAAAsAUU-3'<br>(SEQ ID NO: 9)<br>3'-UUAsGUUUCUUCCUCGACUUUU-5'<br>(SEQ ID NO: 4) |

TABLE 1-continued

| siRNA | Sequences and modified residues |
|---|---|
| ps_P52/gs_P52 | 5'-UCAAAGAAGGAGCUGAAsAsAUU-3'<br>(SEQ ID NO: 10)<br>3'-UUAsGsUUUCUUCCUCGACUUUU-5'<br>(SEQ ID NO: 5) |

(Quantitative Real-Time PCR)

HCV genome copy number was estimated by real-time, quantitative RT-PCR (qRT-PCR) using a primer set and an HCV 5'-UTR-specific TaqMan probe. HCV minus-strand RNA copy number was estimated by a similar method using cDNA synthesized using a forward primer used for real-time PCR quantification of the plus-strand genome copy number. A purified in vitro transcript representing a complementary sequence of HCV 5'-UTR was used as a standard for estimating the copy number of HCV minus-strand RNA. A primer set used for a quantitative RT-PCR analysis on PRK3 mRNA is as follows:

```
Sense primer:
                                (SEQ ID NO: 21)
5'-ATATGGAGCCTAGGACTCGACGTG-3';

Antisense primer:
                                (SEQ ID NO: 22)
5'-AGCTAAGCAGCGGAAGTCCTGA-3'.
```

The synthesized cDNA products were amplified with SYBR Premix Ex Taq (Takara, Shiga, Japan). Target gene levels, normalized to GAPDH were determined using a comparative Ct (ΔΔCt) method (Ahn D G, Lee W et al., *Antiviral Res.* 2011, vol. 91, pp. 1-10). The copy number of a siPRK2-1 guide strand was measured by qRT-PCR using a primer set designed by the manufacturer (Applied Biosystems, Foster City, Calif., USA) and a Taqman probe.

(Immunoprecipitation and Western Blot Analysis)

Immunoprecipitation of PRK1 or PRK2 was performed using an anti-PRK1 or PRK2 antibody. Western blot analyses of immune complexes and cell lysates against HCV NS5B and kinases (PRK1, PRK2, ROCK1, and ROCK2) were performed as disclosed in the article by Kim et al. (*Biochem. Biophys. Res. Commun.* 2012, vol. 421, pp. 112-118).

(MTS Analysis and Cell Cycle Analysis)

The cytotoxicity of the siRNA was measured using a reagent 3-(4,5-dimethylthiazol-2-yl)-2,5-diphenyltetrazolium bromide (MTS). The cell cycle of Huh7 cells transfected with siRNA (50 nM) or treated with LY294002 (50 µM) for 48 hours was analyzed using FACSCalibur flow cytometer (Becton Dickinson, San Jose, Calif., USA).

(Dual Luciferase Reporter Analysis)

A bicistronic dual luciferase vector with a cap-dependent *Renilla* luciferase reporter (RLuc) translation site and an HCV internal ribosome entry site (IRES)-mediated firefly luciferase (FLuc) translation site was transfected into Huh7 cells. At 48 h post-transfection, luciferase activities were quantified using the Dual-Glo luciferase assay system (Promega, Madison, Wis., USA).

(IFN-β Reporter Analysis)

HEK293 cells were transfected with IFNβ-pGL3, which expresses IFN-β promoter controlled FLuc, and pRL-TK reporter (Promega), which expresses RLuc as an internal control. Six hours following transfection, cells were washed and fresh medium was added to the cells. The cells were then transfected with 100 nM siRNA or 1 µg/ml poly(I:C) using Lipofectamine RNAiMAX (Invitrogen). Cells were harvested 8 h following RNA transfection for dual luciferase assays.

(siRNA Stability Test)

The present invention was approved by the Institutional Review Boards of Yonsei University. Human blood was obtained from the Seoul Seobu Red Cross Blood Center of the Korean Red Cross. siRNA (2 µM) was incubated for 4 h at 37° C. in 45% human plasma obtained from healthy donors unless otherwise specified. Total RNA was extracted using Trizol LS reagent (Invitrogen), separated by electrophoresis on a 15% polyacrylamide/7 M urea gel, and electrotransferred to a positively charged nylon membrane (Roche, Basel, Switzerland) for Northern blot analysis. The membrane was UV-crosslinked and probed with a 5'-radiolabeled synthetic ribooligonucleotide complementary to the siPRK2-1 guide strand. The probe was generated using [$\gamma$-$^{32}$P] ATP and T4 polynucleotide kinase (Takara). Densitometric quantification of the radioactive hybridization signal was performed using a Fuji BAS-2500 Phosphorimager.

(Immunohistochemical Analysis of Transplanted Cells)

The xenograft tissues were fixed with 4% paraformaldehyde in PBS and embedded in Frozen Section Compound (Surgipath FSC22, Leica Microsystems, Wetzlar, Germany). Tissue sections (5 µm-thicknesses) were stained with hematoxylin and eosin (H&E) using standard histological techniques or immunostained with a monoclonal mouse anti-HCV core antigen (clone C7-50) and an Alexa fluor 488-conjugated goat anti-mouse IgG antibody (Invitrogen). Nuclei were visualized by 4',6'-diaamidino-2-phenylindole (DAPI) staining and the images were obtained using a LSM 510 META confocal laser scanning microscope (Carl Zeiss, Oberkochen, Germany).

(Cytokine Measurement by ELISA)

The experiment with human peripheral blood mononuclear cells (hPBMCs) was approved by the Institutional Review Board of Yonsei University. hPBMCs were isolated from blood from healthy volunteers (obtained from the Blood Services, Western Blood Center of Korean Red Cross) by ficoll density gradient centrifugation. hPBMCs ($1 \times 10^6$ cells/well) seeded in in a 96-well round-bottom plate were transfected with 10 nM siPRK2-1 or 1 µg poly(I:C) using the lipidoid ND98, or treated with 50 µg/ml poly(I:C) by adding directly to the culture medium (200 µl). hPBMCs were grown in DMED supplemented with 10% FBS, 100 U/ml penicillin and 100 µg/ml streptomycin. After stimulation for 16 h, supernatants were collected by centrifugation. The amounts of IFN-α and TNF-α secreted from the stimulated cells were assessed using the VeriKine human IFN-α (PBL Interferon Source, iscataway, NJ, USA) and TNF-α (ebioscience, San Diego, Calif., USA) enzyme-linked immunosorbent assay (ELISA) kits, respectively. The detection limits of the human IFN-α and TNF-α ELISAs were 15 and 8 pg/ml, respectively.

(Isolation of Mouse Hepatocytes)

Mouse hepatocytes were isolated using a two-step perfusion method and cultured in a collagen-coated culture plate.

(Animal Experiments)

All animal experiments were performed according to the guideline by the Korean Ministry of Food and Drug Safety. A protocol was reviewed and approved by the Yonsei Laboratory Animal Research Center (YLARC) (Permit No: 2012-0076).

(Statistical Analysis)

Data were presented as means±standard deviation (SD) of at least three independent experiments unless otherwise indicated. The significance was analyzed using an unpaired Student's t-test. P values less than 0.05 were considered statistically significant.

(Delivery of siRNAs)

Cells were transfected with the siRNAs using Lipofectamine RNAiMAX (Invitrogen, Carlsbad, Calif., USA) or lipidoid ND98 (98N12-5, see FIG. 6A) according to the manufacturer's manual. siRNA-lipidoid ND98 complex was prepared according to a method disclosed in the article by Akinc A et al. (*Nat Biotechnol* 2008, vol. 26, pp. 561-569).

For in vivo delivery of the siRNA, siRNA lipidoid nanoparticles (LNPs) including ND98, cholesterol (Sigma-Aldrich), PEG 2000-ceramide C16 (Avanti Polar Lipids, Alabaster, Ala., USA) and siRNA were prepared (Akinc A et al., *Nat Biotechnol* 2008, vol. 26, pp. 561-569; Akinc A et al., *Mol Ther* 2009, vol. 17, pp. 872-879), and administered by intratumoral or tail-vein injection (i.v. injection).

(HCV Infection)

The full-length HCV RNA was prepared through in vitro transcription using an HCV JFH1 clone (Wakita T et al., *Nat Med* 2005, vol. 11, pp. 791-796), and electroporated into Huh7 cells to obtain HCV particles. A filtered culture medium was used for injection of the Huh7 cells. Viruses were adsorbed with periodic rocking, washed three times with phosphate-buffered saline (PBS), and then cultured in a complete DMEM.

(Evaluation of In Vivo Anti-HCV Activities of PRK2 siRNA)

The Huh7 cells ($2 \times 10^6$ cells) into which HCV (JFH1) RNA was electroporated were re-suspended in 100 μl of PBS and mixed with 100 μl of Matrigel (BD Biosciences Discovery Labware, Bedford, Mass., USA) before the Huh7 cells were subcutaneously injected to flank regions of an immunodeficient NOD-SCID male mice under anesthesia (5 weeks old, and weighing 20 to 25 g). After 3 weeks of the transplantation, the siPRK2 LNPs (1 mg siRNA/kg) were administered to the established xenograft mice by intratumoral or tail-vein injection. Also, urokinase-type plsaminogen activator-transfected SCID mice (uPA/SCID) having chimeric human/mouse livers (Phoenix Bio Co., Ltd., Hiroshima, Japan) were infected with serum from HCV (genotype 1b) patients. Saline or siPRK2 LNPs were i.v. injected to each of the HCV-infected chimeric mice in the control group (n=3) and the siRNA-treated group (n=3) at a dose of 1-2 mg siRNA/kg.

The HCV titer in the mouse serum was measured by real-time qRT-PCR. A protocol for animal experiments was approved by the Local Institutional Animal Care and Use Committee.

<Experimental Example 1> PRK2 Silencing Effect of siRNA Isotypes

PRK known as a protein kinase N (PKN) is a Ser/Thr kinase in a subfamily of AGC kinases and consists of three isoforms, that is, PRK1, PRK2 and PRK3. To examine whether the HCV replication was specifically regulated by PRK2, siRNAs targeting PRK1, PRK2 or PRK3 were designed and evaluated for anti-HCV activities.

Four PRK2 siRNAs which were considered to be medical supplies and included siPRK2-1 and three other siRNAs (#4, #7 and #9) which actually reduced a level of PRK2 through Western blot analysis on the cells transfected with 10 nM PRK2-specific siRNAs were selected from 11 siRNAs designed to target other regions of a PRK2 mRNA sequence (FIG. 1A).

As shown in FIG. 1C, the siPRK2-1 among the selected siRNAs was most effective in inhibiting the HCV replication; the siRNA (10 nM) delivered by the lipofectamine RNAiMAX reagents reduced an HCV RNA level by about 55% in the R-1 cells harbored with the genotype 1b HCV subgenomic replicon RNA (FIG. 1B).

The Western blot analysis also showed that the steady-state levels of PRK2 and NS5B were reduced by 74% and 60%, respectively, after the PRK2 silencing (FIG. 2A). The siRNAs against the PRK2 isoforms PRK1 and PRK3 or the siRNAs targeting kinases ROCK 1 and ROCK2 irrelevant to the PRK2 isoforms did not inhibit the HCV replication to silence the target kinases (FIGS. 2B to 2E under the same conditions even when used in a higher concentration (50 nM)).

In agreement with the results showing that the PRK1 silencing did not interfere with the HCV replication (FIG. 2B), the co-immunoprecipitation experiment results showed that PRK2 interacted with NS5B (FIG. 3), not PRK1, indicating that there was a specific interaction between PRK2 and NS5B. In addition, the results proved an isotype-specific regulatory role of PRK2 in the HCV replication.

<Experimental Example 2> Effects of PRK2 Silencing on Cell Proliferation or HCV IRES-Dependent Translation 100 nM siPRK2-1 inhibited about 80% of the HCV replication in the R-1 cells, but the non-specific scrambled siRNAs did not significantly inhibit the HCV replication (FIG. 1D). The cell viability measured in this concentration by MTS analysis was not affected by the siRNA treatment (FIG. 4). Based on the reporter analysis, whether the intracellular delivery of the siPRK2-1 induced activation of the IFN-α promoter was evaluated. In this reporter analysis, it was revealed that IRF3 activated by a retinoic acid-inducible gene 1 (RIG-I) or toll-like receptor 3 pathway induced the expression of the luciferase reporter.

The analysis results showed that the siPRK2-1 did not activate the IFN-α promoter, but the synthetic dsRNA poly(I:C) that was a potent activating agent for type-I IFN response known to be recognized by RIG-I increased the activity of the IFN-α promoter activity by three folds (FIG. 1E).

The HCV internal ribosome entry site (IRES)-mediated translation was known to be regulated by the cell cycle. As shown in the results of fluorescence-activated cell sorting analysis, it was revealed that the PRK2 silencing did not change the cell cycle of the Huh7 cells (FIG. 1F). Also, it was revealed that the silencing of PRK2 as well as PRK1 or PRK3 by the siRNA did not inhibit the HCV IRES-dependent translation (FIG. 1G).

In summary, the results indicated that the inhibition of the HCV replication by the PRK2 silencing was not related to the induction of IFN-α production, the disturbance of the cell cycle, or the interference of the IRES-dependent translation.

<Experimental Example 3> Effects of PRK2 Silencing on HCV NS5B Phosphorylation and Roles in HCV RNA Replication As described above, it was proven that PRK2 induced the inhibition of the NS5B phosphorylation. Therefore, the Huh7 cells pre-treated with Sc siRNA or siPRK2-1 were transfected with a Flag-tagged NS5B expression vector and metabolically labeled using [$^{32}$P]-orthophosphate. NS5B was immunoprecipitated in the siRNA-treated cells and analyzed for radioactively labeled and phosphorylated NS5B (p-NS5B). The PRK2 silencing significantly reduced a level of p-NS5B (55%±5.5%, p<0.01; FIG. 5A).

Also, whether the RdRp activity of NS5B had an influence on the inhibition of the phosphorylation by the PRK2 silencing was further examined A Flag-tagged NS5B protein was immunoprecipitated in the siRNA-treated cells having no metabolic label and tested for RdRp activity to a poly (A)/$U_{20}$ substrate. Interestingly, the NS5B of the siPRK2-1-treated cells had a lower RdRp activity compared to the Sc siRNA-treated cells (FIG. 5B), which supported the hypothesis that the NS5B phosphorylation mediated by PRK2 increased the HCV RNA replication. In a recent research, the present inventors have found that the NS5B has two main phosphorylation sites at Ser29 and Ser42. To examine an effect of the NS5B phosphorylation on the HCV replication in vitro, a Ser residue was mutated into Ala to inhibit the NS5B phosphorylation. Thereafter, a replication ability of an HCV (JFH1) mutant was tested in a transient replication analysis.

Similar to the results showing that the reduced NS5B RdRp activity was observed in the cells in which the PRK2 expression was suppressed, the results of experiments in which the HCV replication kinetics were analyzed showed that the HCV had a severely damaged ability to replicate unphosphorylated NS5B. This was comparable to cells expressing inactive NS5B (NS5B_GND) (FIG. 5C) and put an emphasis on the important role in the NS5B phosphorylation in the HCV replication.

<Experimental Example 4> Silencing Effect of Hepatocytes PRK2 by Systemic Delivery of siPRK2-1 Lipidoid Formulation To test an in vivo anti-HCV activity of the siPRK2-1, a lipid-like material, also known as a lipidoid was used. First of all, it was examined whether a first-generation lipidoid ND98 (FIG. 6A) was effective in delivery of the siRNA into hepatocellular carcinoma cells.

As shown in FIG. 6B, this lipidoid effectively delivered the siPRK2-1 as much as the Lipofectamine RNAiMAX did, thereby reducing the intracellular HCV RNA titer in the R-1 cells.

Simple siRNA-lipidoid ioniccomplex was not suitable for in vivo systemic administration of the siRNA since the simple complex had no in vivo stability and had a tendency to form aggregates. Therefore, for the in vivo systemic delivery, the siRNA-lipidoid complex and PEGylated-lipid were formulated using cholesterol, and whether the final siPRK2-1 LNP delivered the siRNA into the hepatocytes which primarily replicated HCV in the livers was tested. The siPRK2-1 LNP was injected once into tail veins of the mice at a dose of 1 mg/kg. To prove a gene silencing effect in the hepatocytes, the mouse hepatocytes were isolated at 48 hour post-siRNA injection by two-step perfusion method and grown overnight to quantify PRK2 mRNA level using qRT-PCR.

As a result, when the LNP-formulated siPRK2-1 was administered once, the PRK2 mRNA level was significantly reduced by 30%, compared to the hepatocytes isolated from the PBS-injected or scrambled siRNA-injected mice of the control group (FIG. 6C).

Accordingly, it could be seen that the LNP effectively delivered the siRNA into the hepatocytes in vivo.

<Experimental Example 5> Effects of siPRK2-1 on HCV Replication in Xenograft Mouse Model An anti-HCV activity of the siPRK2-1 LNP was evaluated in immunodeficient mice in which Huh7 cells transfected with HCV (genotype 2a) RNA by electroporation were subcutaneously xenografted in rear flanks.

After the transfected cells were transplanted, the serum HCV titer was detected at a high level of $1 \times 10^6$-$10^7$ copies/ml 1-2 weeks post-transplantation (FIG. 7A). After xenografting, both of HCV plus- and minus-strand RNAs were detected in the xenograft tissues found from the mice retrieved 4 weeks post-transplantation (FIG. 7B). Therefore, it could be seen that the HCV was replicated in the xenografts.

Also, the results of immunohistochemical analysis showed that an HCV core antigen was expressed in the xenograft tissues (FIG. 7C). When the PRK2 inhibitor HA1077 was intratumorally injected once into the xenograft mice at a dose of 25 mg/kg body weight, it was revealed that the HCV genome level was significantly reduced at the $3^{rd}$ and $5^{th}$ days of the drug administration, indicating that the HA1077 had an in vivo anti-HCV effect (FIG. 7D). From these results, it could also be seen that the xenograft mice producing a high titer of the infectious HCV particles for several weeks were a suitable model for evaluating the in vivo anti-HCV activity of the siPRK2-1.

The non-modified siPRK2-1 encapsulated in LNP was intratumorally injected to the mice at a dose of 1 mg siRNA/kg.

The PRK2 silencing results showed that the serum HCV titer was reduced by 90% at day 5, and the viral titer started to gradually increase at day 7 (FIG. 7E). The HCV titer reached to 37% of the initial HCV titer at day 14.

Also, when the modified siPRK2-1 (ps_siPRK2-1, Table 1) LNPs were injected into the tail veins at a dose of 1 mg/kg to be systemically delivered, the serum HCV RNA titer was observed to be very significantly reduced at day 3 and 7 after administration (FIG. 7F). In the xenograft model, such an anti-viral effect presents that the siPRK2-1 LNPs are not targeted to the hepatocytes by a non-specific, passive method but by the LNP.

The siRNAs formulated into the lipidoid ND98 or LNPs did not substantially induce innate immune responses in the human peripheral blood mononuclear cells when the secreted IFN-α and TNF-α were evaluated using ELISA (FIGS. 8A to 8D).

The results of a preliminary acute toxicity test in the mice treated with siPRK2-1 LNP at a dose of 10 mg/kg showed that no marked acute side effects were observed except a mild edema which completely disappeared within 12 hours after the siRNA injection (not shown). These results present that the siPRK2 LNP has a therapeutic potential since the siPRK2 LNP reduces the HCV titer while having a low toxicity risk.

<Experimental Example 6> PRK2 Silencing Effect Using Chemically Modified siRNAs in Human Hepatocyte-Injected uPA/SCID Mice The half-life of the non-modified siPRK2-1 in human plasma was less than 44 minutes (FIG. 9A).

Chemically modified siRNAs were designed to screen siRNAs whose improved stability and potent gene silencing activity were maintained. A limited number of siRNA duplexes were constructed using modified passenger strands (ps) or guide strands (gs) of siPRK2-1 listed in Table 1, and their serum stabilities were compared. To prove an anti-viral effect in an in vivo experiment as described below, since the stabilities of the chemically modified siRNAs were improved five folds without any loss of the anti-HCV activity, compared to that of the non-modified siRNA, gs_PS1 siRNA having a phosphorothioate bond was selected (FIGS. 9B-D), and the stabilities of the gs_PS1 siPRK2-1 and the non-modified isoform in primary mouse hepatocytes were compared. Since the target sequence of the siPRK2-1 was conserved in the mice, the hepatic stability of the siPRK2-1 in the primary hepatocytes which did not divide for 9 days after the delivery of the lipidoid ND98 into the cells could be tested.

As shown in FIG. 10A, the results of qRT-PCR analysis of the siRNA level remaining in the hepatocytes showed that the intracellular stability of the gs_PS1 siPRK2-1 was improved (at day 6, 178-fold higher abundance). The target gene silencing effect also lasted; the gs_PS1 siPRK2-1 had an improved target silencing ability at day 9 after transfection of the siRNA, compared to the non-modified siRNA (FIG. 10B; 69% to 50% for the non-modified siRNA and gs_PS1 siRNA).

In the BALB/c mice (n=3) to which the modified siRNA was i.v. injected at a dose of 1 mg siRNA/kg, an in vivo distribution profile of the siRNA was evaluated by Northern blotting, and most of the delivered siRNAs (approximately 95%) were observed to be targeted to the livers (FIG. 10C). It was revealed that the delivered siRNAs were uniformly distributed in four main liver lobes accounting for 81% of the total livers.

The anti-HCV activity of the siPRK2-1 LNP was tested in the livers of the immunodeficient chimeric mice to which the human hepatocytes were transplanted. The gs_PS1 siPRK2-1 LNPs were i.v. injected into the tail veins at a dose of 2 mg/kg.

As shown in FIG. 10D, when the siPRK2-1 LNPs were administered once, the serum HCV genome titer was reduced by 92% on day 2. The reduced HCV genome titer gradually increased to a starting level within 5 days after the siRNA administration. On the other hand, a decrease in the serum HCV RNA titer was not observed in the PBS-treated control group. In one mouse to which the siRNA nanoparticles were injected twice at a dose of 1 mg/kg every three days, the genome titer was reduced by less than 88% on day 2, and the silencing effect lasted longer, until day 6, indicating that a multiple dosing schedule may prolong PRK2 silencing and further improve the anti-HCV effect.

No significant body weight changes were observed in the siRNA-treated mice (FIG. 10E), indicating that little in vivo toxicity of the siRNA formulation at least under these dosing schedules.

Next, when the modified gs_PS1 LNPs were continuously administered three times at a dose of 3 mg/kg every three days to be systemically delivered, a significantly reduced serum HCV RNA titer ((3.72 log 10±0.12 log 10 SD, $p<0.0001$; FIG. 11A) was observed. In summary, these results prove an effect of the PRK2 silencing on the HCV RNA replication in vivo.

Then, in an orthotopic mouse model in which the Huh7 cells in which HCV was replicated were directly transplanted to the livers of the immunodeficient NOD-SCID mice, an anti-HCV effect of the gs_PS1 siPRK2-1 was tested. At 4 weeks post-xenografting, both of the plus (+) and minus (−) strands of the HCV genome were detected in the transplanted tissues (FIG. 11B).

The presence of the HCV genome was further confirmed through Northern blotting. Based on the immunohistochemical analysis results, it was revealed that the transplanted Huh7 cells were positively stained for HCV NS5B and human CD81 that was a main HCV entry factor (FIG. 11C).

To prove an ability of NLP to deliver the siRNA to the livers, the anti-HCV ability of the gs_PS1 siPRK2-1 LNP was evaluated in the orthotopic xenograft mouse model. When the gs_PS1 siPRK2-1 LNP was systemically administered at a dose of 3 mg/kg (injected once every 3 days for three times total), the serum HCV genome titer was reduced by 1.96 log 10±0.72 log 10 ($p<0.0001$) and by a maximum of 2.77 log 10, but a significant decrease in the serum HCV RNA titer in the Sc siRNA-treated control group was not observed (FIG. 11D).

As in the subcutaneous xenograft model, the results explicitly show that the anti-HCV potential of the siPRK2-1 LNP is proven in vivo.

INDUSTRIAL APPLICABILITY

The siRNA according to one embodiment of the present invention or a lipid formulation thereof can be used as a hepatitis C therapeutic agent.

The invention claimed is:

1. A double-stranded small interfering RNA (siRNA) which has 15 to 30 base pairs, targets a nucleotide sequence region of PRK2 mRNA set forth in SEQ ID NO: 1 and consists of a guide strand and a passenger strand, wherein the guide strand has a complementary sequence to a consecutive base sequence of at least 15 base pairs in the targeted base sequence.

2. The siRNA of claim 1, wherein the siRNA consists of a guide strand sequence set forth in SEQ ID NO: 2 and a passenger strand sequence set forth in SEQ ID NO: 3.

3. The siRNA of claim 1, wherein the siRNA has a chemically modified glucose or a base structure in one or more ribonucleic acids or has a chemically modified binding site between the ribonucleic acids, wherein the chemical modification comprises at least one selected from the group consisting of:
 a) a modification of a phosphodiester bond at the 3' or 5' terminus or both termini thereof into a boranophosphate or phosphorothioate bond;
 b) an introduction of an ethylene-bridged nucleic acid (ENA) onto the 3' or 5' terminus or both termini thereof; and
 c) a substitution of a hydroxyl group (—OH) at a 2' position of a ribose ring with at least one selected from the group consisting of —NH$_2$ (amino group), —C-allyl (allyl group), —F (fluoro group), and —O-Me (methyl group).

4. The siRNA of claim 3, wherein the chemically modified siRNA consists of:
 one guide strand having a base sequence set forth in SEQ ID NO: 4 or 5; and
 one passenger strand having a base sequence set forth in SEQ ID NO: 3, 9 or 10.

5. An expression vector comprising the siRNA defined in claim 1.

6. The expression vector of claim 5, wherein the expression vector is selected from the group consisting of a plasmid, an adeno-associated viral vector, a retroviral vector, a vaccinia viral vector, and an oncolytic adenoviral vector.

7. A composition for treating hepatitis C comprising the siRNA defined in claim 1.

8. The composition of claim 7, wherein the siRNA is included in the form of a complex with a nucleic acid delivery system.

9. The composition of claim 8, wherein the nucleic acid delivery system is selected from the group consisting of a viral vector, a non-viral vector, a liposome, a cationic polymer, a micelle, an emulsion, and solid lipid nanoparticles.

10. The composition of claim 7, further comprising at least one anti-HCV agent for combined administration selected from the group consisting of:
 1) at least one HCV non-structural protein inhibitor selected from the group consisting of NS2, NS3, NS4A, NS4B, NS5A, and NS5B;
 2) at least one HCV structural protein inhibitor selected from the group consisting of capsid protein C, an envelope glycoprotein E1 or E2, and a p7 protein;
 3) at least one broad-spectrum anti-viral agent selected from the group consisting of IFN-α and ribavirin;
 4) at least one HCV gene inhibitor selected from the group consisting of an HCV internal ribosome entry site (IRES), a capsid protein C-coding gene, an HCV 3'-untranslated region (3'-UTR), and a conserved region of a consensus sequence in HCV genotypes; and
 5) at least one host target gene inhibitor for controlling the replication or proliferation of HCV selected from the group consisting of PRK2, Hsp90, PDK1, CD81, and a host factor binding to an HCV structural or non-structural protein.

11. A method of treating hepatitis C, comprising:
 administering a pharmaceutically effective amount of the siRNA defined in claim 1 to a subject in need thereof.

12. The method of claim 11, wherein the siRNA is administered in the form of a complex with a nucleic acid delivery system.

13. The method of claim 12, wherein the nucleic acid delivery system is selected from the group consisting of a viral vector, a non-viral vector, a liposome, a cationic polymer, a micelle, an emulsion, and solid lipid nanoparticles.

14. The method of claim 11, further comprising administering at least one anti-HCV agent for combined administration selected from the group consisting of:
 1) at least one HCV non-structural protein inhibitor selected from the group consisting of NS2, NS3, NS4A, NS4B, NS5A, and NS5B;
 2) at least one HCV structural protein inhibitor selected from the group consisting of capsid protein C, an envelope glycoprotein E1 or E2, and a p7 protein;
 3) at least one broad-spectrum anti-viral agent selected from the group consisting of IFN-α and ribavirin;
 4) at least one HCV gene inhibitor selected from the group consisting of an HCV internal ribosome entry site (IRES), a capsid protein C-coding gene, an HCV 3'-untranslated region (3'-UTR), and a conserved region of a consensus sequence in HCV genotypes; and
 5) at least one host target gene inhibitor for controlling the replication or proliferation of HCV selected from the group consisting of PRK2, Hsp90, PDK1, CD81, and a host factor binding to a HCV structural or non-structural protein.

\* \* \* \* \*

SEQUENCE LISTING

```
<160> NUMBER OF SEQ ID NOS: 26

<210> SEQ ID NO 1
<211> LENGTH: 19
<212> TYPE: RNA
<213> ORGANISM: Artificial Sequence
<220> FEATURE:
<223> OTHER INFORMATION: PRK2 mRNA 527-545 nt

<400> SEQUENCE: 1
ucaaagaagg agcugaaaa                                                  19

<210> SEQ ID NO 2
<211> LENGTH: 21
<212> TYPE: RNA
<213> ORGANISM: Artificial Sequence
<220> FEATURE:
```

```
<223> OTHER INFORMATION: siPRK2-1 guide strand

<400> SEQUENCE: 2
uuuucagcuc cuucuuugau u                                              21

<210> SEQ ID NO 3
<211> LENGTH: 21
<212> TYPE: RNA
<213> ORGANISM: Artificial Sequence
<220> FEATURE:
<223> OTHER INFORMATION: siPRK2-1 passenger strand

<400> SEQUENCE: 3
ucaaagaagg agcugaaaau u                                              21

<210> SEQ ID NO 4
<211> LENGTH: 21
<212> TYPE: RNA
<213> ORGANISM: Artificial Sequence
<220> FEATURE:
<223> OTHER INFORMATION: gs_PS1 siPRK2-1 modified guide strand
<220> FEATURE:
<221> NAME/KEY: conflict
<222> LOCATION: (18)..(19)
<223> OTHER INFORMATION: Between base G and A, modification is
      introduced by replacing one non-bridging oxygen atom on the
      backbone phosphate between two ribonucleotides with a sulfur atom
      to create a phosphorothioate(PS) linkage.

<400> SEQUENCE: 4
uuuucagcuc cuucuuugau u                                              21

<210> SEQ ID NO 5
<211> LENGTH: 21
<212> TYPE: RNA
<213> ORGANISM: Artificial Sequence
<220> FEATURE:
<223> OTHER INFORMATION: gs_PS2 siPRK2-1 modified guide strand
<220> FEATURE:
<221> NAME/KEY: conflict
<222> LOCATION: (17)..(19)
<223> OTHER INFORMATION: Between base U and G, and G and A, modification
      is introduced by replacing one non-bridging oxygen atom on the
      backbone phosphate between two ribonucleotides with a sulfur atom
      to create a phosphorothioate(PS) linkage.

<400> SEQUENCE: 5
uuuucagcuc cuucuuugau u                                              21

<210> SEQ ID NO 6
<211> LENGTH: 21
<212> TYPE: RNA
<213> ORGANISM: Artificial Sequence
<220> FEATURE:
<223> OTHER INFORMATION: ps_2'O-Me modified passenger strand
<220> FEATURE:
<221> NAME/KEY: modified_base
<222> LOCATION: (1)..(21)
<223> OTHER INFORMATION: ps_2'O-Me modified passenger strand is the
      siPRK2-1 passenger strand chemically modified by substituting
      2'-O-methyl group for hydroxyl group at C2 position of all ribose.

<400> SEQUENCE: 6
ucaaagaagg agcugaaaau u                                              21

<210> SEQ ID NO 7
<211> LENGTH: 21
<212> TYPE: RNA
<213> ORGANISM: Artificial Sequence
```

```
<220> FEATURE:
<223> OTHER INFORMATION: gs_All-F modified guide strand
<220> FEATURE:
<221> NAME/KEY: modified_base
<222> LOCATION: (1)..(21)
<223> OTHER INFORMATION: gs_All-F modified guide strand is the siPRK2-1
      guide strand chemically modified by substituting fluoro group for
      hydroxyl group at C2 position of all ribose.

<400> SEQUENCE: 7
uuuucagcuc cuucuuugau u                                              21

<210> SEQ ID NO 8
<211> LENGTH: 21
<212> TYPE: RNA
<213> ORGANISM: Artificial Sequence
<220> FEATURE:
<223> OTHER INFORMATION: gs_Py-F modified guide strand
<220> FEATURE:
<221> NAME/KEY: modified_base
<222> LOCATION: (1)..(21)
<223> OTHER INFORMATION: gs_Py-F modified guide strand is the siPRK2-1
      guide strand chemically modified by substituting fluoro group for
      hydroxyl group at C2 position of ribose of pyrimidine.

<400> SEQUENCE: 8
uuuucagcuc cuucuuugau u                                              21

<210> SEQ ID NO 9
<211> LENGTH: 21
<212> TYPE: RNA
<213> ORGANISM: Artificial Sequence
<220> FEATURE:
<223> OTHER INFORMATION: ps_PS1 modified passenger strand
<220> FEATURE:
<221> NAME/KEY: conflict
<222> LOCATION: (18)..(19)
<223> OTHER INFORMATION: Between base A and A, modification is
      introduced by replacing one non-bridging oxygen atom on the
      backbone phosphate between two ribonucleotides with a sulfur atom
      to create a phosphorothioate(PS) linkage.

<400> SEQUENCE: 9
ucaaagaagg agcugaaaau u                                              21

<210> SEQ ID NO 10
<211> LENGTH: 21
<212> TYPE: RNA
<213> ORGANISM: Artificial Sequence
<220> FEATURE:
<223> OTHER INFORMATION: ps_PS2 modified passenger strand
<220> FEATURE:
<221> NAME/KEY: conflict
<222> LOCATION: (17)..(19)
<223> OTHER INFORMATION: Between base A and A, and A and A, modification
      is introduced by replacing one non-bridging oxygen atom on the
      backbone phosphate between two ribonucleotides with a sulfur atom
      to create a phosphorothioate(PS) linkage.

<400> SEQUENCE: 10
ucaaagaagg agcugaaaau u                                              21

<210> SEQ ID NO 11
<211> LENGTH: 21
<212> TYPE: RNA
<213> ORGANISM: Artificial Sequence
<220> FEATURE:
<223> OTHER INFORMATION: siPRK1-1 guide strand for silencing PRK1
      isoform
<220> FEATURE:
<221> NAME/KEY: variation
```

-continued

```
<222> LOCATION: (20)..(21)
<223> OTHER INFORMATION: UU are substituted with thymines(TT).

<400> SEQUENCE: 11
gaugauguca aucuuggucu u                                              21

<210> SEQ ID NO 12
<211> LENGTH: 21
<212> TYPE: RNA
<213> ORGANISM: Artificial Sequence
<220> FEATURE:
<223> OTHER INFORMATION: siPRK1-2 guide strand for silencing PRK1
      isoform
<220> FEATURE:
<221> NAME/KEY: variation
<222> LOCATION: (20)..(21)
<223> OTHER INFORMATION: UU are substituted with thymines(TT).

<400> SEQUENCE: 12
gcuguagguc uggaucaugu u                                              21

<210> SEQ ID NO 13
<211> LENGTH: 21
<212> TYPE: RNA
<213> ORGANISM: Artificial Sequence
<220> FEATURE:
<223> OTHER INFORMATION: siPRK3-1 guide strand for silencing PRK3
      isoform
<220> FEATURE:
<221> NAME/KEY: variation
<222> LOCATION: (20)..(21)
<223> OTHER INFORMATION: UU are substituted with thymines(TT).

<400> SEQUENCE: 13
aagcaguuuc accacguucu u                                              21

<210> SEQ ID NO 14
<211> LENGTH: 21
<212> TYPE: RNA
<213> ORGANISM: Artificial Sequence
<220> FEATURE:
<223> OTHER INFORMATION: siPRK3-2 guide strand for silencing PRK3
      isoform
<220> FEATURE:
<221> NAME/KEY: variation
<222> LOCATION: (20)..(21)
<223> OTHER INFORMATION: UU are substituted with thymines(TT).

<400> SEQUENCE: 14
cuccugcuuc uucagugcuu u                                              21

<210> SEQ ID NO 15
<211> LENGTH: 21
<212> TYPE: RNA
<213> ORGANISM: Artificial Sequence
<220> FEATURE:
<223> OTHER INFORMATION: siROCK1-1 guide strand for silencing ROCK1
<220> FEATURE:
<221> NAME/KEY: variation
<222> LOCATION: (20)..(21)
<223> OTHER INFORMATION: UU are substituted with thymines(TT).

<400> SEQUENCE: 15
gcagcagguu guccauuuuu u                                              21

<210> SEQ ID NO 16
<211> LENGTH: 21
<212> TYPE: RNA
<213> ORGANISM: Artificial Sequence
```

```
<220> FEATURE:
<223> OTHER INFORMATION: siROCK1-2 guide strand for silencing ROCK1
<220> FEATURE:
<221> NAME/KEY: variation
<222> LOCATION: (20)..(21)
<223> OTHER INFORMATION: UU are substituted with thymines(TT).

<400> SEQUENCE: 16
gcaaacaauc cgaauucacu u                                           21

<210> SEQ ID NO 17
<211> LENGTH: 21
<212> TYPE: RNA
<213> ORGANISM: Artificial Sequence
<220> FEATURE:
<223> OTHER INFORMATION: siROCK2-1 guide strand for silencing ROCK2
<220> FEATURE:
<221> NAME/KEY: variation
<222> LOCATION: (20)..(21)
<223> OTHER INFORMATION: UU are substituted with thymines(TT).

<400> SEQUENCE: 17
uccccgcccc ucagucagau u                                           21

<210> SEQ ID NO 18
<211> LENGTH: 21
<212> TYPE: RNA
<213> ORGANISM: Artificial Sequence
<220> FEATURE:
<223> OTHER INFORMATION: siROCK2-2 guide strand for silencing ROCK2
<220> FEATURE:
<221> NAME/KEY: variation
<222> LOCATION: (20)..(21)
<223> OTHER INFORMATION: UU are substituted with thymines(TT).

<400> SEQUENCE: 18
gccugccucu agcuccggcu u                                           21

<210> SEQ ID NO 19
<211> LENGTH: 21
<212> TYPE: RNA
<213> ORGANISM: Artificial Sequence
<220> FEATURE:
<223> OTHER INFORMATION: scrambled siRNA

<400> SEQUENCE: 19
guucagcgug uccggcgagu u                                           21

<210> SEQ ID NO 20
<211> LENGTH: 21
<212> TYPE: RNA
<213> ORGANISM: Artificial Sequence
<220> FEATURE:
<223> OTHER INFORMATION: scrambled siRNA

<400> SEQUENCE: 20
cucgccggac acgcugaacu u                                           21

<210> SEQ ID NO 21
<211> LENGTH: 24
<212> TYPE: DNA
<213> ORGANISM: Artificial Sequence
<220> FEATURE:
<223> OTHER INFORMATION: Sense primer for RT-PCR

<400> SEQUENCE: 21
atatggagcc taggactcga cgtg                                        24
```

```
<210> SEQ ID NO 22
<211> LENGTH: 22
<212> TYPE: DNA
<213> ORGANISM: Artificial Sequence
<220> FEATURE:
<223> OTHER INFORMATION: Antisense primer for RT-PCR

<400> SEQUENCE: 22
agctaagcag cggaagtcct ga                                              22

<210> SEQ ID NO 23
<211> LENGTH: 12
<212> TYPE: PRT
<213> ORGANISM: Homo sapiens
<220> FEATURE:
<221> NAME/KEY: SIMILAR
<222> LOCATION: (1)..(12)
<223> OTHER INFORMATION: PRK1 512-523 a.a

<400> SEQUENCE: 23

Val Ala Thr Trp Val Arg Leu Leu Arg Arg Leu Ile
1               5                   10

<210> SEQ ID NO 24
<211> LENGTH: 12
<212> TYPE: PRT
<213> ORGANISM: Homo sapiens
<220> FEATURE:
<221> NAME/KEY: SIMILAR
<222> LOCATION: (1)..(12)
<223> OTHER INFORMATION: PRK2 514-525 a.a

<400> SEQUENCE: 24

Ile Ala Thr Trp Gly Arg Leu Val Arg Arg Ala Ile
1               5                   10

<210> SEQ ID NO 25
<211> LENGTH: 12
<212> TYPE: PRT
<213> ORGANISM: Homo sapiens
<220> FEATURE:
<221> NAME/KEY: SIMILAR
<222> LOCATION: (1)..(12)
<223> OTHER INFORMATION: PRK3 451-462 a.a

<400> SEQUENCE: 25

Met Ala Ala Trp Gly Arg Leu Val Met Asn Leu Leu
1               5                   10

<210> SEQ ID NO 26
<211> LENGTH: 12
<212> TYPE: PRT
<213> ORGANISM: Hepatitis C virus
<220> FEATURE:
<221> NAME/KEY: SIMILAR
<222> LOCATION: (1)..(12)
<223> OTHER INFORMATION: NS5B peptide region binding to PRK isozyme

<400> SEQUENCE: 26

Thr Ser Thr Ala Gly Arg Ile Val Arg Arg Ala Ile
1               5                   10
```